United States Patent
Eisenbach-Schwartz et al.

(10) Patent No.: US 6,267,955 B1
(45) Date of Patent: *Jul. 31, 2001

(54) MONONUCLEAR PHAGOCYTES AND THEIR USE TO PROMOTE AXONAL REGENERATION

(75) Inventors: Michal Eisenbach-Schwartz; Orly Spiegler, both of Rehovot (IL); David L. Hirschberg, Menlo Park, CA (US)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

This patent is subject to a terminal disclaimer.

(21) Appl. No.: 09/041,280

(22) Filed: Mar. 11, 1998

Related U.S. Application Data

(63) Continuation-in-part of application No. 08/818,818, filed on Mar. 14, 1997, now Pat. No. 6,117,424, which is a continuation-in-part of application No. 08/695,351, filed on Aug. 9, 1996, now Pat. No. 5,800,812, which is a continuation-in-part of application No. 08/528,845, filed on Sep. 15, 1995, now abandoned.

(51) Int. Cl.[7] .................................................. A01N 63/00
(52) U.S. Cl. ..................... 424/93.71; 424/93.7; 424/520; 424/570
(58) Field of Search ............................... 424/93.7, 93.71, 424/520, 570

(56) References Cited

U.S. PATENT DOCUMENTS

| | | |
|---|---|---|
| 5,078,996 | 1/1992 | Conlon et al. . |
| 5,082,670 | 1/1992 | Gage et al. . |
| 5,157,024 | 10/1992 | Gordon . |

FOREIGN PATENT DOCUMENTS

| | | |
|---|---|---|
| 0 172 987 A2 | 3/1986 | (EP) . |
| 0 415 321 A1 | 3/1991 | (EP) . |
| 0 501 445 A1 | 9/1992 | (EP) . |
| WO 97/09885 | 3/1997 | (WO) . |
| WO 97/26901 | 7/1997 | (WO) . |

OTHER PUBLICATIONS

Barrett et al., 1989, "Relation of macrophage activity to axonal regeneration in the injured spinal cord", Soc. Neurosci. Abstr. 15:317 (Abstract No. 125.12).

Barrett et al., 1990, "Activation of macrophages stimulates axonal regeneration in the injured spinal cord", Anat. Rec. 226:11A (Abstract).

Blaugrund et al., 1992, "Disappearances of astrocytes and invasion of macrophages following crush injury of adult rodent optic nerves: Implications for regeneration", Exp Neurol 118:105–115.

Blaugrund et al., 1993, "Axonal Regeneration Is Associated With Glial Migration: Comparison Between the Injured Optic Nerves of Fish and Rats", Journal of Comparative Neurology 330:105–112.

Chamak and Mallat, 1993, "Regulation of neurite growth and regeneration by brain macrophages: Involvement of thrombospondin", J Neurochem 61(Suppl.):S99 (Abstract #280018–3).

Chamak et al., 1994, "Brain macrophages stimulate neurite growth and regeneration by secreting thrombospondin", J Neurosci Res 38:221–233.

Cohen et al., 1990, "Oligodendrocyte cytotoxic factor associated with fish optic nerve regeneration: implications for mammalian CNS regeneration", Brain Research 537:24–32.

Danon et al., 1989, "Promotion of wound repair in old mice by local injection of macrophages," Proc. Natl. Acad. Sci. USA 86:2018–2020.

David et al., 1990, "Macrophages can modify the nonpermissive nature of the adult mammalian central nervous system", Neuron 5:463–469.

Eitan and Schwartz, 1993, "A Transglutaminase That Converts Interleukin–2 into a Factor Cytotoxic to Oligodendrocytes", Science 261:106–108.

Eitan et al., 1992, "Identification of an interleukin 2–like substance as a factor cytotoxic to oligodendrocytes and associated with central nervous sytem regeneration", Proc. Natl. Acad. Sci. USA 89:5442–5446.

Eitan et al., 1994, "Recovery of visual response of injured adult rat optic nerves treated with transglutaminase", Science 264:1764–1768.

Frisen et al., 1994, "Adhesive/repulsive properties in the injured spinal cord: Relation to myelin phagocytosis by invading macrophages", Exp Neurol 129:183–193.

George and Griffin, 1994, "Delayed macrophage responses and myelin clearance during Wallerian degeneration in the central nervous system: The dorsal radiculotomy model", Exp Neurol 129:225–236.

Giulian and Robertson, 1990, "Inhibition of mononuclear phagocytes reduces ischemic injury in the spinal cord", Ann Neurol 27:33–42.

(List continued on next page.)

Primary Examiner—Marianne P. Allen
(74) Attorney, Agent, or Firm—Browdy and Neimark

(57) ABSTRACT

Methods and compositions are disclosed for the use of allogeneic mononuclear phagocytes to promote axonal regeneration in the central nervous system of a mammal. In one embodiment, allogeneic mononuclear phagocytes are cultured together with stimulatory tissue, such as skin, dermis or at least one nerve segment, and are subsequently administered into the central nervous system of a mammal at or near a site of injury or disease. In an alternative embodiment, autologous monocytes, preferably stimulated autologous monocytes, are administered into the central nervous system of a mammal at or near a site of injury or disease. CNS administration of mononuclear phagocytes may optionally be combined with administration of an adjuvant factor (e.g. aFGF) to the CNS, anti-inflammatory therapy of the mammal, or both. Methods for screening stimulatory tissue and cells and methods and compositions for cryopreserved allogeneic mononuclear phagocytes are also disclosed.

46 Claims, 18 Drawing Sheets

OTHER PUBLICATIONS

Figure 1:
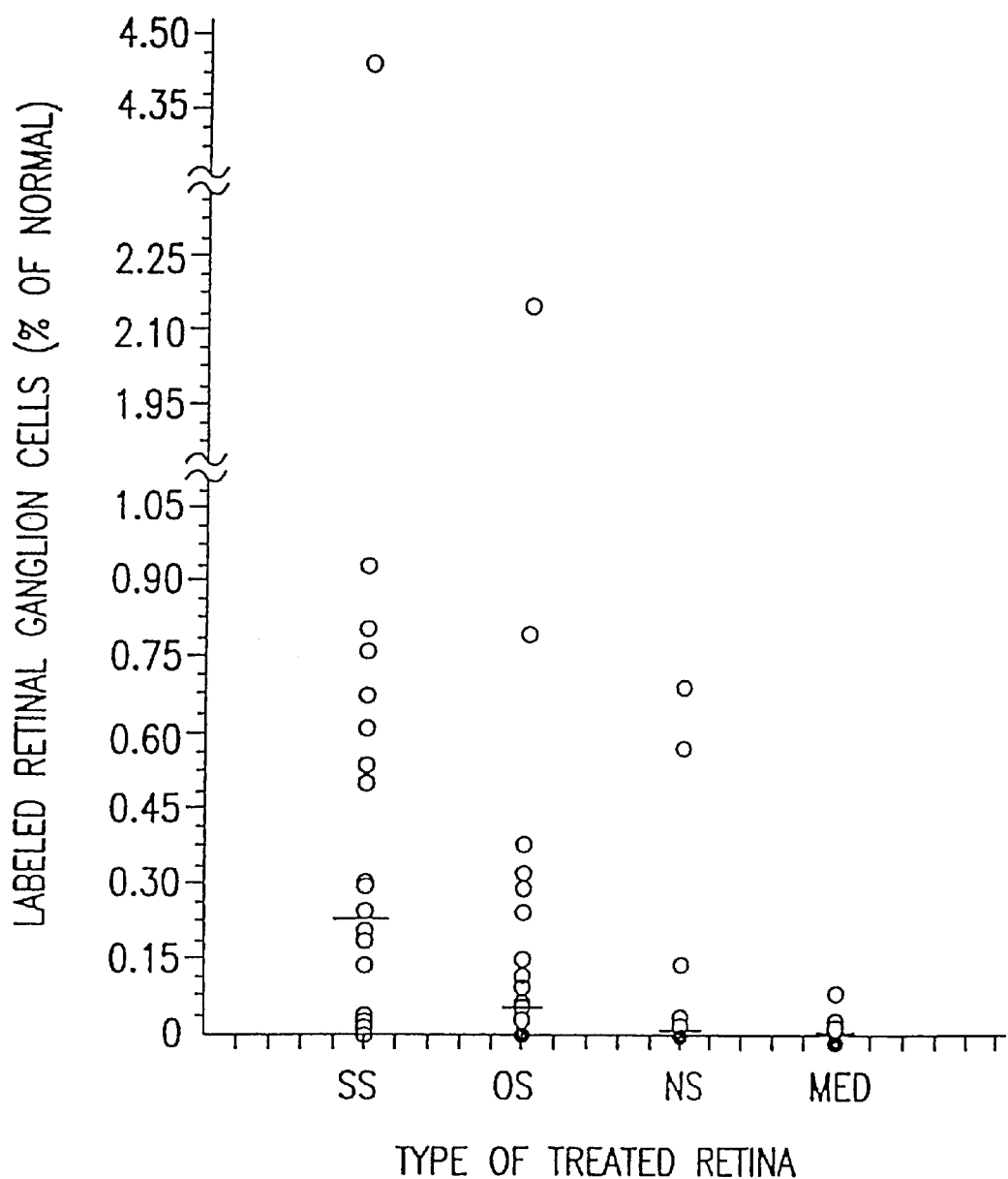

Griffin et al., 1992, "Macrophage responses and myelin clearance during Wallerian degeneration: Relevance to immune mediated demyelination", J Immunol 40:153–166.

Heumann et al., 1987, "Differential regulation of mRNA encoding nerve growth factor and its receptor in rat sciatic nerve during development, degeneration, and regeneration: Role of macrophages", Proc. Natl. Acad. Sci. USA 84:8735–8739.

Hirschberg and Schwartz, 1995, "Macrophage recruitment to acutely injured central nervous system is inhibited by a resident factor: a basis for an immune–brain barrier", Journal of Neuroimmunology 61:89–96.

Hirschberg et al., 1994, "Inflammation after axonal injury has conflicting consequences for recovery of function: Rescue of spared axons is impaired but regeneration is supported", J Neuroimmunol 50:9–16.

Hirschberg et al., 1995, "Bidirectional communication between the macrophage and the nerve after injury", 9th Int'l Cong. Immunology, San Francisco (Abstract No. 1646).

Ignatius et al., 1986, "Expression of apolipoprotein E during nerve degeneration and regeneration", Proc. Natl. Acad. Sci. USA 83:1125–1129.

Jackowski, 1995, "Neural injury repair: hope for the future as barriers to effective CNS regeneration become clearer", British J. Neurosurgery 9:303–317.

Khan and Wigley, 1994, "Different effects of a macrophage cytokine on proliferation in astrocytes and Schwann cells", NeuroReport 5:1381–1385.

Lavie et al., 1987, "Morphological response of injured adult rabbit optic nerve to implants containing media conditioned by growing optic nerves", Brain Research 419:166–172.

Lazarov–Spiegler et al., 1996, "Transplantation of activated macrophages overcomes central nervous system regrowth failure", FASEB J. 10:1296–1302.

Lazarov–Spiegler et al., 1996, "Transplantation of activated macrophages overcomes central nervous system regrowth failure", Soc. Neurosci. Abstr. 22(2):1232 (Abstr. # 490.21).

Lotan and Schwartz, 1994, "Cross talk between the immune system and the nervous system in response to injury: Implications for regeneration", FASEB J 8:1026–1033.

Lotan et al., 1994, "Cytokines modulate the inflammatory response and change permissiveness to neuronal adhesion in injured mammalian central nervous system", Exp Neurol 126:284–290.

Lu and Richardson, 1991, "Inflammation near the Nerve Cell Body Enhances Axonal Regeneration", J. Neuroscience 11:972–978.

Mallat et al., 1989, "Lipopolysaccharide–stimulated rat brain macrophages release NGF in vitro", Develop Biol 133:309–311.

Patrick et al., 1996, "Quantitative Effects of Peripheral Monocytes and Nerve Growth Factor on CNS Neural Morphometric Outgrowth Parameters in Vitro," Exp. Neurology 138:277–285.

Pennell et al., 1995, "Depletion of major histocompatibility complex (MHC)–bearing cells from embryonic rat spinal cord", Society for Neuroscience Abstracts 21:823 (Abstract No. 330.18).

Perry and Brown, 1992, "Role of macrophages in peripheral nerve degeneration and repair", BioEssays 14(6):401–406.

Perry and Brown, 1992, "Macrophages and nerve regeneration", Curr. Op. Neurobiol. 2:679–682.

Perry and Gordon, 1991, "Macrophages and the Nervous System", International Review of Cytology 125:203–244.

Perry et al., 1987, "The Macrophage Response to Central and Peripheral Nerve Injury A Possible Role for Macrophage in Regeneration", J. Exp. Med. 165:1218–1223.

Rabchevsky et al., 1993, "Transplantation of fluorescently––labeled microglia into the adult rat spinal cord", Society for Neuroscience Abstracts 19:57 (Abstract No. 32.14).

Rabchevsky et al., 1994, "Intraspinal transplantation of enriched microglia seeded within biodegradable polymeric tubes: Evidence for neuritic ingrowth", Society for Neuroscience Abstracts 20:879 (Abstract No. 367.11).

Rabchevsky et al., 1995, "Transplantation of brain macrophages (BrM) embedded in gelfoam into the injured rat spinal cord: Evidence for neuritic ingrowth and the presence of extracellular matrix", J. Neurotrauma 12:136 (Abstract).

Schwartz, 1987, "Molecular and cellular aspects of nerve regeneration", CRC Critical Rev Biochem 22(2):89–110.

Schwartz, 1993, "New light on nerve regeneration in the mammalian nervous system", Endeavour 17(1):38–40.

Schwartz et al., 1989, "Dichotomy of the glial cell response to axonal injury and regeneration", FASEB J 3:2371–2378.

Schwartz et al., 1992, "Tumor Necrosis Factor and TNF–Like Factors in Central Nervous System Regeneration", in Tumor Necrosis Factor: Structure–Function Relationships and Clinical Application (Osawa and Bonavida, eds.), pp. 135–143.

Schwartz et al., 1994, "Cytokines and cytokine–related substances regulating glial cell response to injury of the central nervous system", Progress in Brain Research 103:331–341.

Schwartz et al., 1995, "Central nervous system regeneration and the immune system", Molec. Medicine Today 1:60.

Schwartz et al., 1995, "CNS repair, remyelination and growth factors" J. Neuroimmunology 0 (Suppl. 1):11 (Abstract).

Schwartz et al., 1996, "Potential Treatment Modalities for Glaucomatous Neuropathy: Neuroprotection and Neuroregeneration", J. Glaucoma 5:427–432.

Sivron and Schwartz, 1994, "Nonpermissive nature of fish optic nerves to axonal growth is due to presence of myelin–associated growth inhibitors", Exp Neurol 130:411–413.

Sivron et al., 1991, "Soluble factor(s) produced in injured fish optic nerve regulate the postinjury number of oligodendrocytes: Possible role of macrophages", GLIA 4:591–601.

Stoll et al., 1989, "Wallerian degeneration in the peripheral nervous system: participation of both Schwann cells and macrophages in myelin degradation", Journal of Neurocytology 18:671–683.

Suzuki, (publication date unknown), "Experimental pathology of developing nervous system", NIH Grant No. R01 NS24453–09, Grant application dated Feb. 25, 1994. (Listed in Federal Research in Progress database).

Thomas, 1992, "Brain macrophages: Evaluation of microglia and their functions", Brain Res Rev 17:61–74.

Vick et al., 1992, "Role of adult oligodendrocytes in remyelination after neural injury", J Neurotrauma 9(Supp 1):S93–S103.

Lazarov–Spiegler et al., 1997, "Transplantation of activated macrophages induces axonal regrowth following injury", Soc. Neurosci. Abstr. 23:1995 (Abstract No. 777.5).

Bellingan et al., 1996, "In Vivo Fate Of The Inflammatory Macrophage During The Resolution Of Inflammation", J. Immunol. 157:2577–2585.

Cheng et al., 1996, "Spinal Cord Repair In Adult Paraplegic Rats: Partial Restoration Of Hind Limb Function", Science 273:510–513.

Davies et al., 1997, "Regeneration Of Adult Axons In White Matter Tracts Of The Central Nervous System", Nature 390:680–683.

Faber–Elman et al., 1996, "Involvement Of Wound–Associated Factors In Rat Brain Astrocyte Migratory Response To Axonal Injury: In Vitro Simulation", J. Clin. Invest. 97:162–171.

Fitch and Silver, 1997, "Activated Macrophages And The Blood–Brain Barrier: Inflammation After CNS Injury Leads To Increases In Putative Inhibitory Molecules", Exp. Neurology 148:587–603.

Franzen et al., 1998, "Effects Of Macrophage Transplantation In The Injured Adult Rat Spinal Cord: A Combined Immunocytochemical And Biochemical Study", J. Neuroscience Res. 51:316–327.

Genovesi et al., 1989, "In Vitro Induction Of Swine Peripheral Blood Monocyte Proliferation By The Fibroblast–Derived Murine Hematopoietic Growth Factor CSF–1", Vet. Immunol. Immunopathol. 23:223–244.

Grill et al., 1997, "Cellular Delivery Of Neutrotrophin–3 Promotes Corticospinal Axonal Growth And Partial Functional Recovery After Spinal Cord Injury", J. Neuroscience 17:5560–5572.

Hikawa and Takenaka, 1996, "Myelin–Stimulated Macrophages Release Neutrotrophic Factors For Adult Dorsal Root Ganglion Neurons In Culture", Cell. Mol. Neurobiology 16:517–528.*

Hoffman et al., 1993, "Characterization Of The Immunosuppressive Effects Of Nitric Oxide In Graft vs Host Disease", J. Immunol. 151:1508–1518.*

Li et al., 1997, "Repair Of Adult Rat Corticospinal Tract By Transplants Of Olfactory Ensheathing Cells", Science 277:2000–2002.*

Prewitt et al., 1997, "Activated Macrophage/Microglial Cells Can Promote The Regeneration Of Sensory Axons Into The Injured Spinal Cord", Exp. Neurology 148:433–443.*

Rabchevsky and Streit, 1997, "Grafting Of Cultured Microglial Cells Into The Lesioned Spinal Cord Of Adult Rats Enhances Neurite Outgrowth", J. Neuroscience Res. 47:34–48.*

Schwab and Bartholdi, 1996, "Degeneration And Regeneration Of Axons In The Lesioned Spinal Cord", Physiolog. Rev. 76:319–370.*

Travis, 1997, "Repairing Severed Spinal Cords", Technology Rev. May/Jun. pp. 13–14.*

Xu et al., 1997, "Bridging Schwann Cell Transplants Promote Axonal Regeneration From Both The Rostral And Caudal Stumps Of Transected Adult Rat Spinal Cord", J. Neurocytology 26:1–16.*

Ye and Houle, 1997, "Treatment Of The Chronically Injured Spinal Cord With Neurotrophic Factors Can Promote Axonal Regeneration From Supraspinal Neurons", Exp. Neurology 143:70–81.*

Young, 1997, "Fear Of Hope", Science 277:1907.*

Young, 1996, "Spinal Cord Regeneration", Science 273:451.*

Wray et al., 1993, "Characterization of the Suprachiasmic Nucleus in Organotypic Slice Explant Cultures", Microscopy Research And Techniques 25: 46–60.

* cited by examiner

FIG. 3A
FIG. 3B

475 μm

MONONUCLEAR PHAGOCYTES AND THEIR USE TO PROMOTE AXONAL REGENERATION

This is a continuation-in-part of application Ser. No. 08/818,818, filed Mar. 14, 1997, now U.S. Pat. No. 6,117,424 which is a continuation-in-part of application Ser. No. 08/695,351, filed Aug. 9, 1996, now U.S. Pat. No. 5,800,812 which in turn is a continuation-in-part of application Ser. No. 08/528,845, filed Sep. 15, 1995 (now abandoned), each of which is incorporated herein by reference in its entirety.

1. FIELD OF THE INVENTION

The present invention relates to compositions comprising mononuclear phagocytes, and to methods for using mononuclear phagocytes, to promote axonal regeneration in mammals affected by injury or disease of the central nervous system, as well as to compositions and methods for enhancing the therapeutic capacity of mononuclear phagocytes to promote axonal regeneration. In particular, the invention relates to (a) pharmaceutical compositions comprising, and methods for administering, stimulated or non-stimulated allogeneic mononuclear phagocytes at or near a site of the mammalian central nervous system affected by injury or disease to promote axonal regeneration, (b) compositions and methods for stimulating mononuclear phagocytes so as to enhance their capacity to promote axonal regeneration, and (c) methods for screening tissues, cells, proteins, peptides and other biologically active agents for their ability to stimulate mononuclear phagocytes for promoting axonal regeneration.

2. BACKGROUND OF THE INVENTION

Following axonal injury, neurons of the mammalian central nervous system (CNS) have a poor capacity for axonal regeneration. By contrast, neurons of the mammalian peripheral nervous system (PNS) have a substantially greater capacity for axonal regeneration. See Schwartz et al., 1989, FASEB J. 3:2371–2378.

The difference between axonal regeneration in the CNS and PNS has been attributed to the cellular environment of the neurons rather than to the neurons themselves. Following neuronal injury, the Schwann cells that surround PNS neurons are modulated so as to become permissive or supportive for axonal regeneration. By contrast, the astrocytes, oligodendrocytes and microglia that surround CNS neurons do not show such modulation and remain unsupportive or inhibitory for axonal regeneration. See Schwartz et al., 1987, CRC Crit. Rev. Biochem. 22:89–110.

This lack of modulation has been correlated with differences in the post-injury inflammatory response. See Perry and Brown, 1992, Bioessays 14:401–406; Lotan and Schwartz, 1994, FASEB J. 8:1026–1033. In particular, the accumulation of mononuclear phagocytes in response to CNS injury is delayed and limited in comparison with the response to injury in the PNS. This limited CNS mononuclear phagocyte response may in turn lead to (1) inefficient removal of the myelin debris that reportedly inhibits axonal regeneration, and (2) suboptimal release of macrophage-derived cytokines that would promote modulation of astrocytes and oligodendrocytes so as to support axonal regeneration.

The above observations have prompted speculation that appropriate modulation of the macrophage response might promote axonal regeneration after CNS injury. In an in vitro system, David et al. showed that when cryostat sections of normal rat optic nerve are co-cultured with mononuclear phagocytes derived from lesions of the rat CNS, the optic nerve sections show enhanced adhesiveness for embryonic chick dorsal root ganglion cells. David et al., 1990, Neuron 5:463–469. Conditioned medium from activated peritoneal macrophages was also effective in promoting adhesiveness of optic nerve sections in this in vitro assay.

However, results derived from in vivo models of CNS injury have revealed that some interventions that enhance the macrophage response to CNS injury do not result in enhanced regeneration. For instance, local injection of either tumor necrosis factor alpha (TNF-$\alpha$) or colony stimulating factor-1 (CSF-1) enhanced the macrophage response to experimental optic nerve injury. However, only TNF-$\alpha$, but not CSF-1, increased the permissiveness of the injured optic nerves for neuronal adhesion as assayed in vitro. Lotan et al., 1984, Exp. Neurol. 126:284–290. It has been suggested as one possible explanation that "only appropriately stimulated macrophages can influence neuronal regeneration." Schwartz et al., 1994, Progress Brain Res. 103:331–341, at 338.

In fact, contrary to the teaching of the present invention, other investigators have reported that mononuclear phagocytes might exacerbate damage or limit recovery following CNS injury. Brain macrophages, when stimulated by cytokines, exhibit neurotoxic activity. Chamak et al., 1994, J. Neurosci. Res. 38:221–233. Pharmacological inhibition of mononuclear phagocyte function has been reported to promote recovery in a rabbit model of spinal cord injury. Giulian and Robertson, 1990, Annals Neurol. 27:33–42. It has been suggested that macrophage-derived cytokines may promote formation of glial scars and thereby inhibit axonal regeneration. Khan and Wigley, 1994, NeuroReport 5:1381–1385; Vick et al., 1992, J. Neurotrauma 9:S93–S103.

Citation or identification of any reference in Section 2 (or any other section) of this application shall not be construed as an admission that such reference is available as prior art to the present invention.

3. SUMMARY OF THE INVENTION

The present invention is directed to methods, and compositions, for use of allogeneic mononuclear phagocytes to promote axonal regeneration in the central nervous system of a mammal. The allogeneic mononuclear phagocytes are administered into the CNS at or near a site of injury or disease.

Allogeneic mononuclear phagocytes useful for the methods and compositions of the invention include, but are not limited to, allogeneic monocytes, macrophages and dendritic cells, and autologous monocytes, macrophages and dendritic cells.

The present invention further provides methods, and compositions, for stimulating allogeneic mononuclear phagocytes so as to enhance their capacity to promote axonal regeneration, and methods and compositions for use of stimulated allogeneic mononuclear phagocytes to promote axonal regeneration in the central nervous system of a mammal. The mononuclear phagocytes are stimulated by culturing them together with suitable tissue or suitable cells, or by culturing the mononuclear phagocytes in medium that has been conditioned by suitable tissue or suitable cells. Tissues suitable for this purpose include, without limitation, nerve segments (especially segments of peripheral nerve), dermis, synovial tissue, tendon sheath, liver, and other regenerating tissues. Skin obtained by punch biopsy is especially preferred for this purpose. Alternatively, the mononuclear phagocytes are stimulated by culturing them in medium to which at least one suitable biologically active agent has been added. Biologically active agents suitable for this purpose include, without limitation, neuropeptides; cytokines, for instance transforming growth factor-$\beta$ (TGF-$\beta$), $\beta$-interferon (IFN-$\beta$), $\gamma$-interferon (IFN-$\gamma$), tumor necrosis factor $\alpha$ (TNF-$\alpha$), interleukin 2 (IL-2), interleukin 3 (IL-3), interleukin 4 (IL-4), interleukin 10 (IL-10) and monocyte chemotactic and activating factor (MCAF); colony stimulating factors, for instance macrophage colony stimulating factor (M-CSF), granulocyte-macrophage colony stimulating factor (GM-CSF) and colony stimulating factor 1 (CSF-1); neurotrophic factors, for instance neurotrophic factor 3 (NT-3), nerve growth factor (NGF) and brain-derived neurotrophic factor (BDNF); and other biologically active molecules, for instance lipid A, the tripeptide fMet-Leu-Phe (fMLP), muramyl dipeptide (MDP), the ionophore A23187, and vitamin D3 binding protein. A biologically active protein or peptide may be used in its native or recombinant form.

CNS administration of mononuclear phagocytes may optionally be combined with administration of an adjuvant factor (e.g. aFGF) to the CNS, anti-inflammatory therapy of the mammal, or both.

The present invention further provides an assay for screening or identifying additional tissues, cells and biologically active agents that are suitable for stimulating mononuclear phagocytes to enhance their capacity to promote axonal regeneration. According to this assay, mononuclear phagocytes are first cultured together with the tissue or cells to be tested, or in medium that has been conditioned by the tissue or cells to be tested or in medium to which has been added the biologically active agent to be tested. The cultured mononuclear phagocytes are then assayed for phagocytic activity, nitric oxide production, or both these activities. Mononuclear phagocytes with increased phagocytic activity, increased production of nitric oxide, or both, have an enhanced capacity to promote axonal regeneration.

4. BRIEF DESCRIPTION OF THE FIGURES

The present invention may be more fully understood by reference to the following detailed description of the invention, examples of specific embodiments of the invention and the appended figures in which:

FIG. 1 illustrates axonal regeneration in transected optic nerves of rats as detected by retrograde transport of fluorescent dye to retinal ganglion cells (RGCs). See text, Section 6, for experimental details. Shortly after transection, 2 $\mu$l of DCCM-1 medium were applied to the site of injury containing no cells (MED); $2.5 \times 10^3 - 1 \times 10^5$ non-stimulated (NS) monocytes; $2.5 \times 10^3 - 1 \times 10^5$ optic nerve-stimulated (OS) monocytes; or $2.5 \times 10^3 1 \times 10^5$ sciatic nerve-stimulated (SS) monocytes. Open circles represent individual experimental animals. Solid circles represent animals that showed no labeled RGCs (numbering 7, 7 and 6 in the MED, NS and OS treatment groups respectively). Horizontal lines represent the median value of each treatment group.

Figure 2:
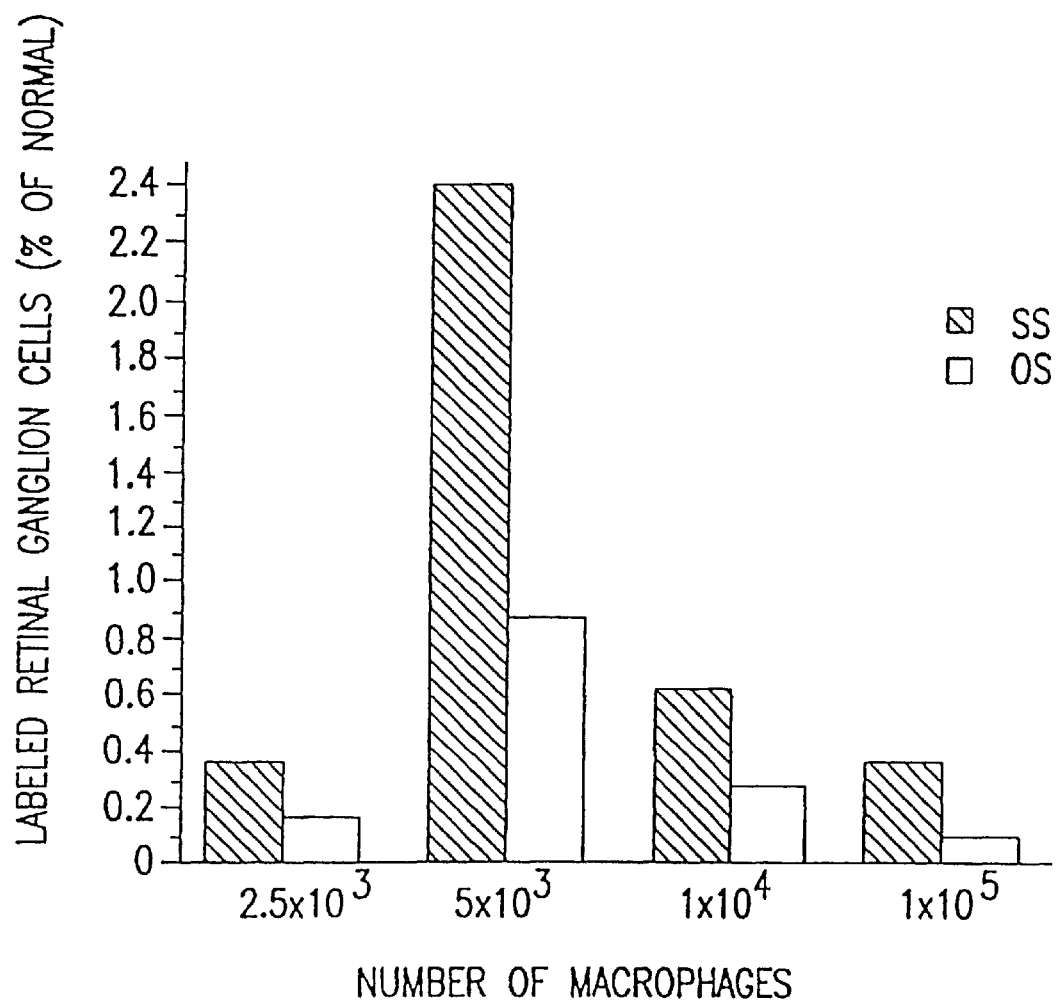
Figure 4A:
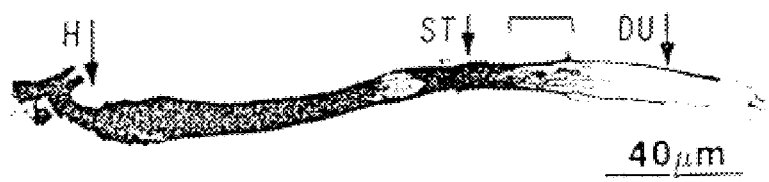
Figure 4B:
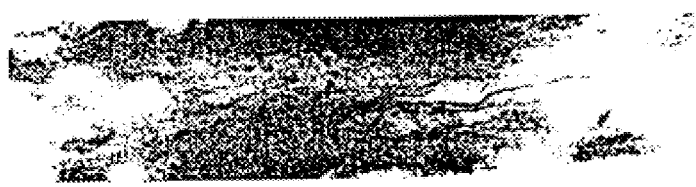
Figure 4C:
Figure 4D:
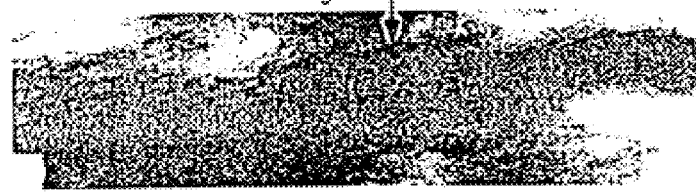
Figure 4E:

FIG. 2 illustrates axonal regeneration in transected optic nerves of rats as a function of the number and type of monocytes applied to the site of injury shortly after transection. See text, Section 6, for experimental details. At the time of transection, 2 $\mu$l DCCM-1 medium were applied to the site of injury containing optic nerve-stimulated monocytes (OS) or sciatic nerve-stimulated monocytes (SS) at a total dose of $2.5 \times 10^3$ cells; $5 \times 10^3$ cells; $10^4$ cells; or $10^5$ cells.

FIGS. 3(A–B) present representative photomicrographs showing retrograde labeling of retinal ganglion cells in rats subjected to optic nerve transection followed by administration of (A) $5 \times 10^3$ sciatic nerve-stimulated monocytes or (B) control medium. See text, Section 6, for experimental details.

FIGS. 4(A–E) present representative photomicrographs showing anterograde labeling of optic nerve fibers in rats subjected to optic nerve transection followed by administration of sciatic nerve-stimulated monocytes (A–D) or control medium (E). See text, Section 6, for experimental details. FIG. 4A is a low magnification view showing the point at which HRP was applied (H), the site of transection (ST) and the surrounding dura mater (DU). The bracketed region, distal to the site of transection, is shown at higher magnification in FIGS. 4B, 4C and 4D, in which growth cone-like structures (gc) are shown at the tips of the fibers.

Figure 5:
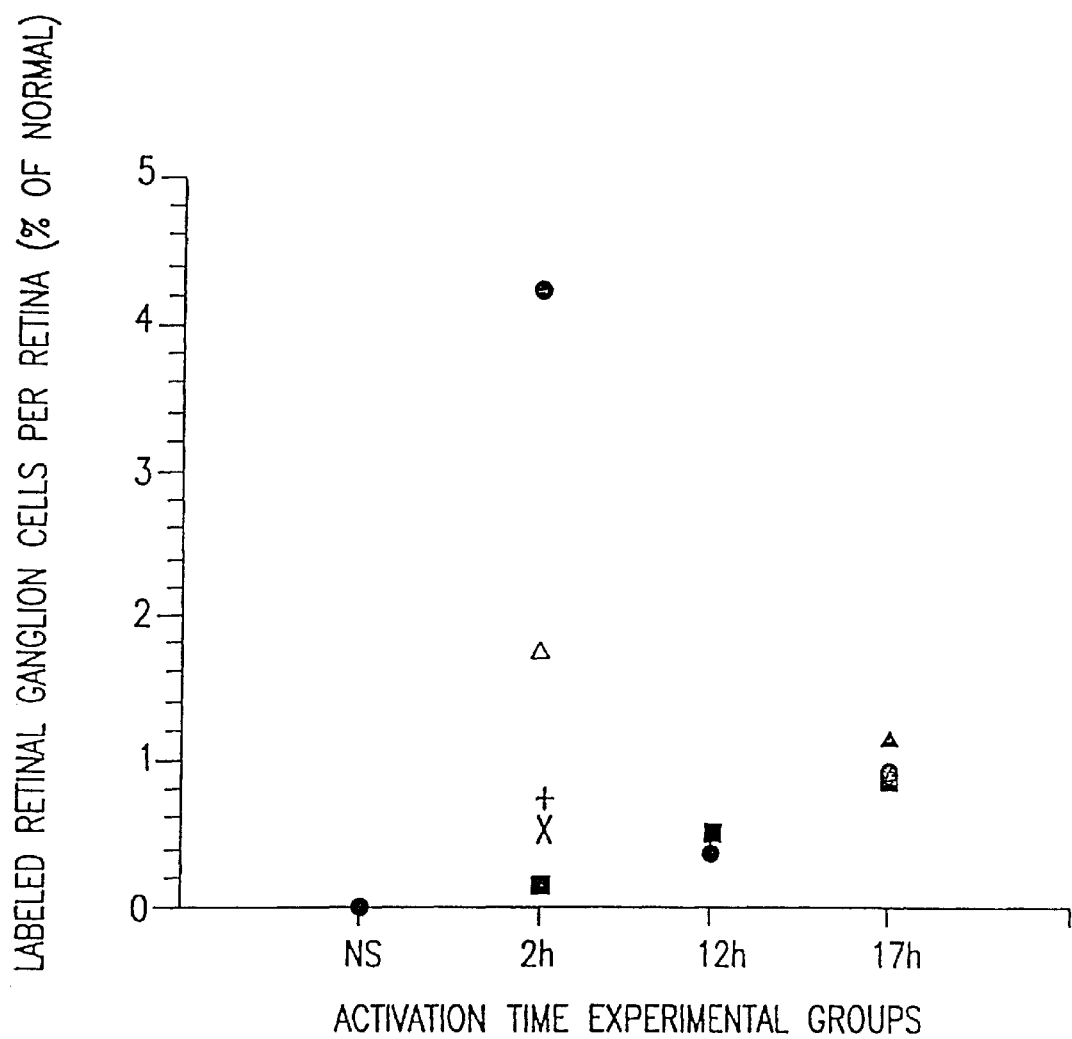

FIG. 5 illustrates axonal regeneration in transected optic nerves of rats after application to the site of injury of monocytes cultured with sciatic nerve for 2–17 hours. See text, Section 6, for experimental details. At the time of transection, 2 $\mu$l of DCCM-1 medium were applied to the site of injury containing $5 \times 10^3$ non-stimulated monocytes (NS) or $5 \times 10^3$ monocytes cultured with rat sciatic nerve for 2 hours (2 h), 12 hours (12 h) or 17 hours (17 h).

Figure 6:
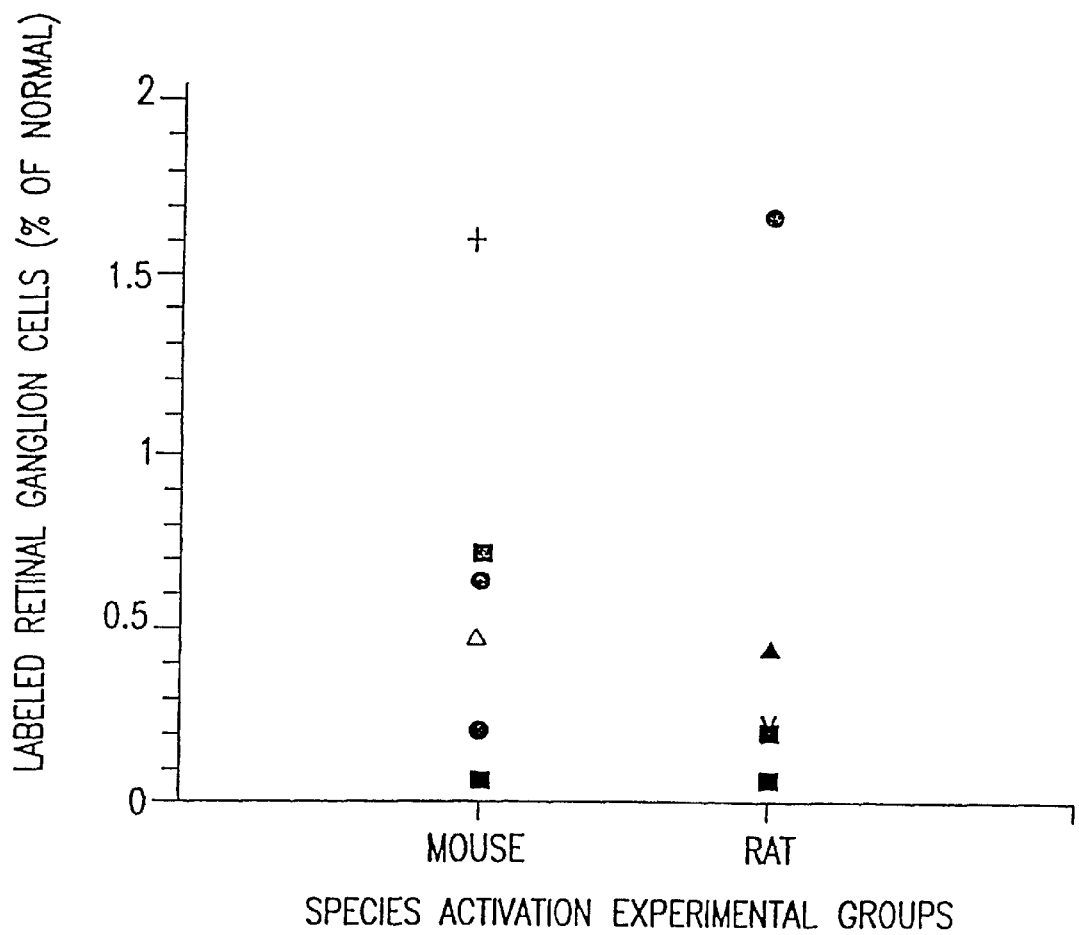

FIG. 6 illustrates axonal regeneration in transected optic nerves after administration, at the site of injury, of rat monocytes stimulated with mouse sciatic nerve or rat sciatic nerve. See text, Section 6, for experimental details. At the time of transection, 2 $\mu$l DCCM-1 medium were applied to the site of injury containing $5 \times 10^3$ monocytes cultured for 24 hours with either mouse sciatic nerve (MOUSE) or rat sciatic nerve (RAT).

Figure 7:
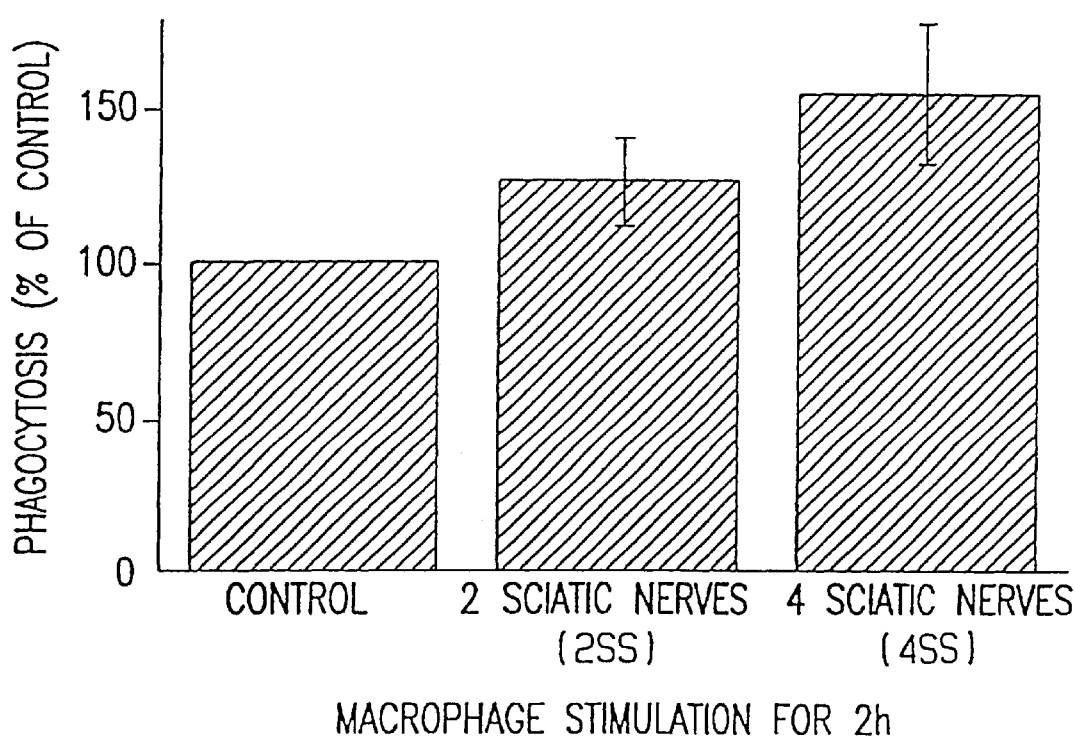

FIG. 7 illustrates the phagocytic activity of rat monocytes cultured for 2 hours with rat sciatic nerve. See text, Section 6, for experimental details. $2.5 \times 10^5$ rat monocytes were cultured in 1 ml DCCM-1 medium alone (CONTROL) or in 1 ml DCCM-1 medium with 2 segments of rat sciatic nerve (2SS) or with 4 segments of rat sciatic nerve (4SS). After 2 hours, the monocytes were exposed to fluorescent beads and cell-associated fluorescence was measured by flow cytometry.

Figure 8:
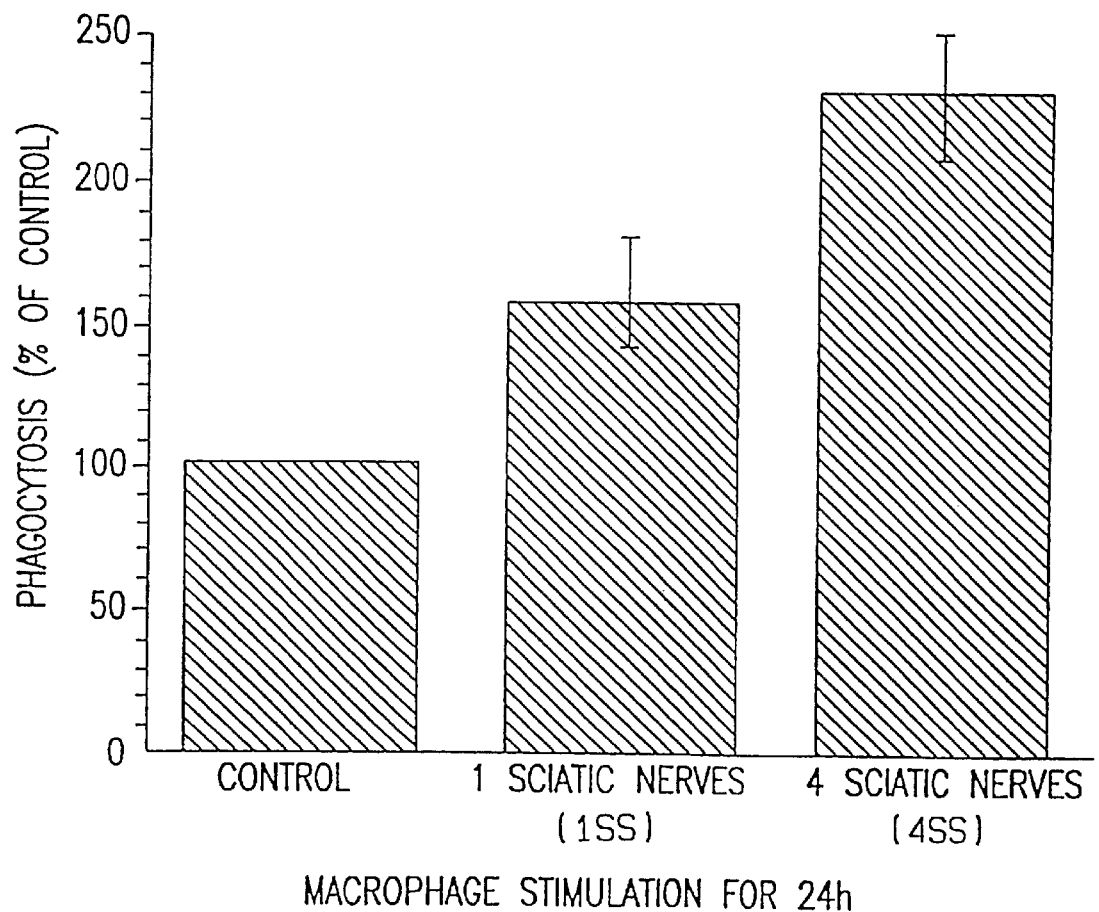

FIG. 8 illustrates the phagocytic activity of rat monocytes cultured for 24 hours with rat sciatic nerve. See text, Section 6, for experimental details. $2.5 \times 10^5$ rat monocytes were cultured in 1 ml DCCM-1 medium alone (CONTROL) or in 1 ml DCCM-1 medium with 1 segment of rat sciatic nerve (1SS) or with 4 segments of rat sciatic nerve (4SS). After 16–24 hours, the monocytes were exposed to fluorescent beads and cell-associated fluorescence was measured by flow cytometry.

Figure 9:
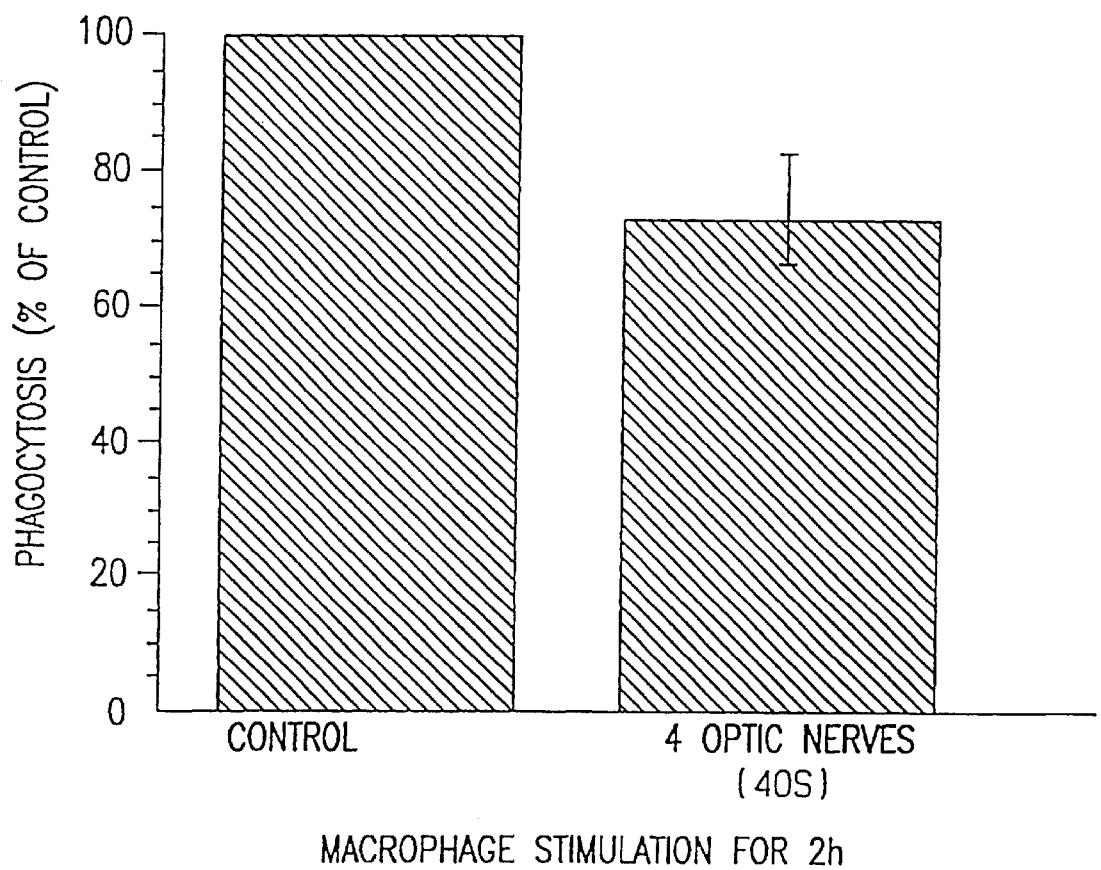

FIG. 9 illustrates the phagocytic activity of rat monocytes cultured for 2 hours with rat optic nerve. See text, Section 6, for experimental details. $2.5 \times 10^5$ rat monocytes were cultured in 1 ml DCCM-1 medium alone (CONTROL) or in 1 ml DCCM-1 medium with 4 segments of rat optic nerve (4OS). After 2 hours, the monocytes were exposed to fluorescent beads and cell-associated fluorescence was measured by flow cytometry.

Figure 10:
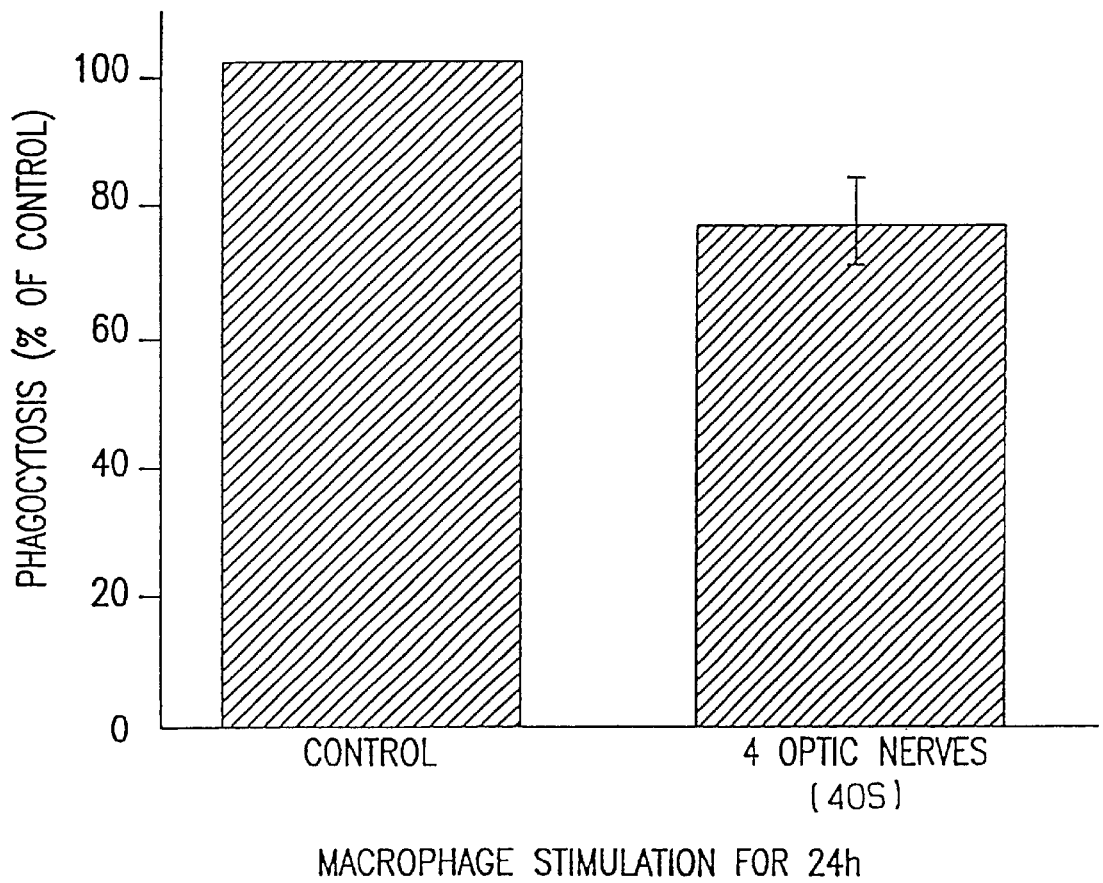

FIG. 10 illustrates the phagocytic activity of rat monocytes cultured for 24 hours with rat optic nerve. See text, Section 6, for experimental details. $2.5 \times 10^5$ rat monocytes were cultured in 1 ml DCCM-1 medium alone (CONTROL) or in 1 ml DCCM-1 medium with 4 segments of rat optic nerve (4OS). After 24 hours, the monocytes were exposed to fluorescent beads and cell-associated fluorescence was measured by flow cytometry.

Figure 11:
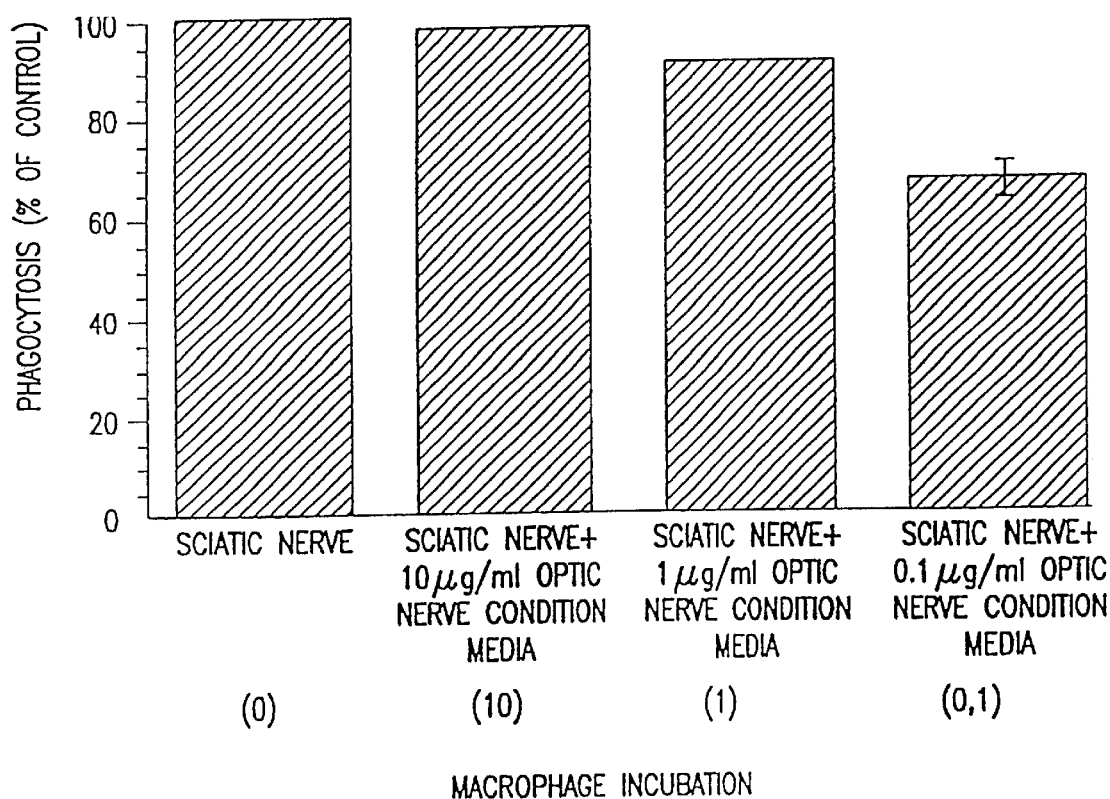

FIG. 11 illustrates the phagocytic activity of rat monocytes cultured overnight with rat sciatic nerve in the presence of medium conditioned by rat optic nerve. $5 \times 10^5$ rat monocytes were cultured in 1 ml DCCM-1 medium with 6 segments of rat sciatic nerve with no further additions (0) or with the addition of optic nerve-conditioned medium at a total protein concentration of 0.1 µg/ml (0.1), 1.0 µg/ml (1), or 10 µg/ml (10). After 24 hours, the monocytes were exposed to fluorescent beads and cell-associated fluorescence was measured by flow cytometry.

Figure 12:
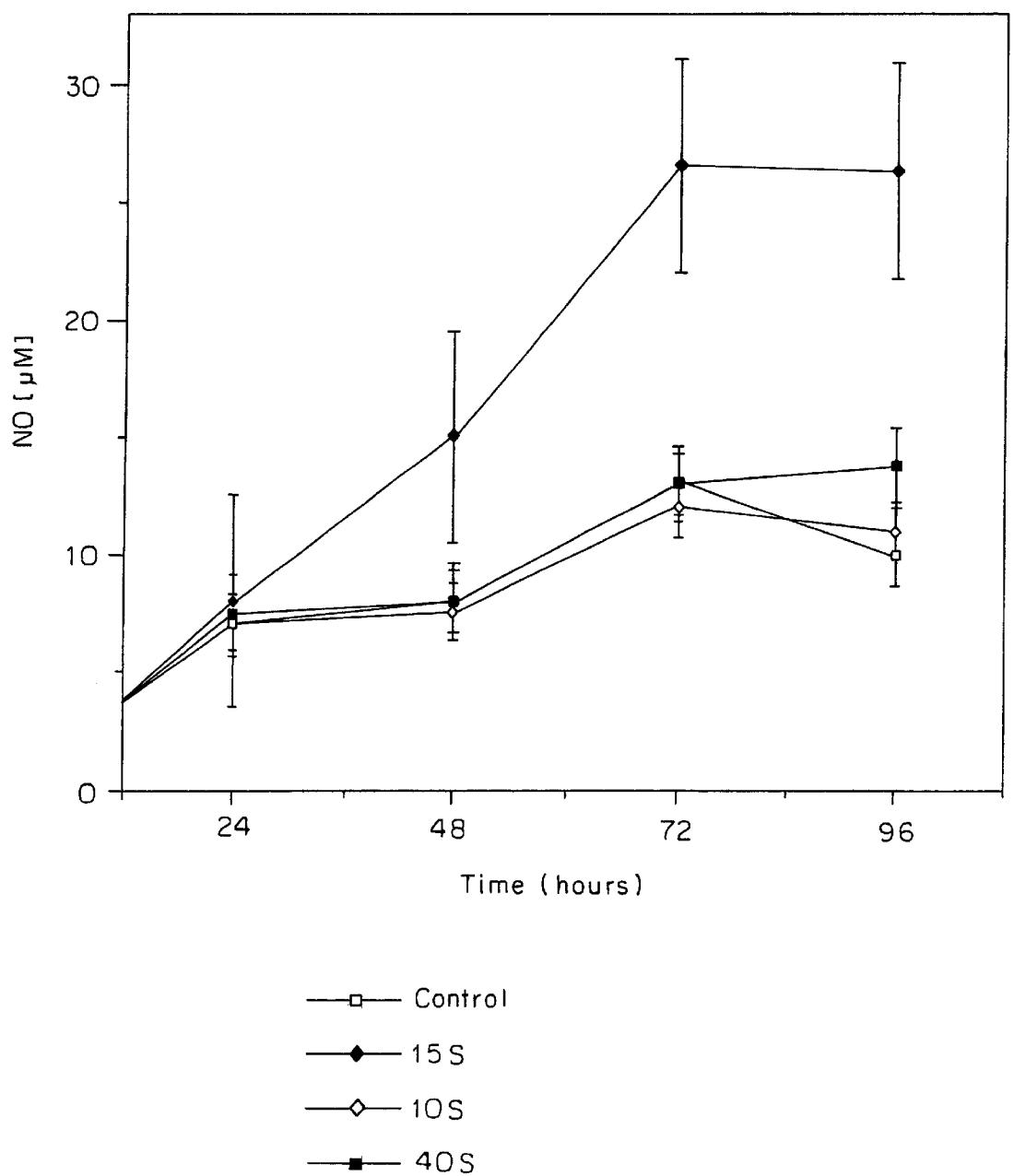

FIG. 12 illustrates nitric oxide production by rat monocytes cultured for 24, 48, 72 or 96 hours with rat sciatic nerve or with rat optic nerve. See text, Section 6, for experimental details. $10^6$ rat monocytes were cultured in 1 ml DCCM-1 medium alone (CONTROL), or in the same medium with 1 segment of rat sciatic nerve (1SS), with 1 segment of rat optic nerve (1OS), or with four segments or rat optic nerve (4OS). After 24, 48, 72 or 96 hours, the media were collected and the levels of nitric oxide were measured.

Figure 13:
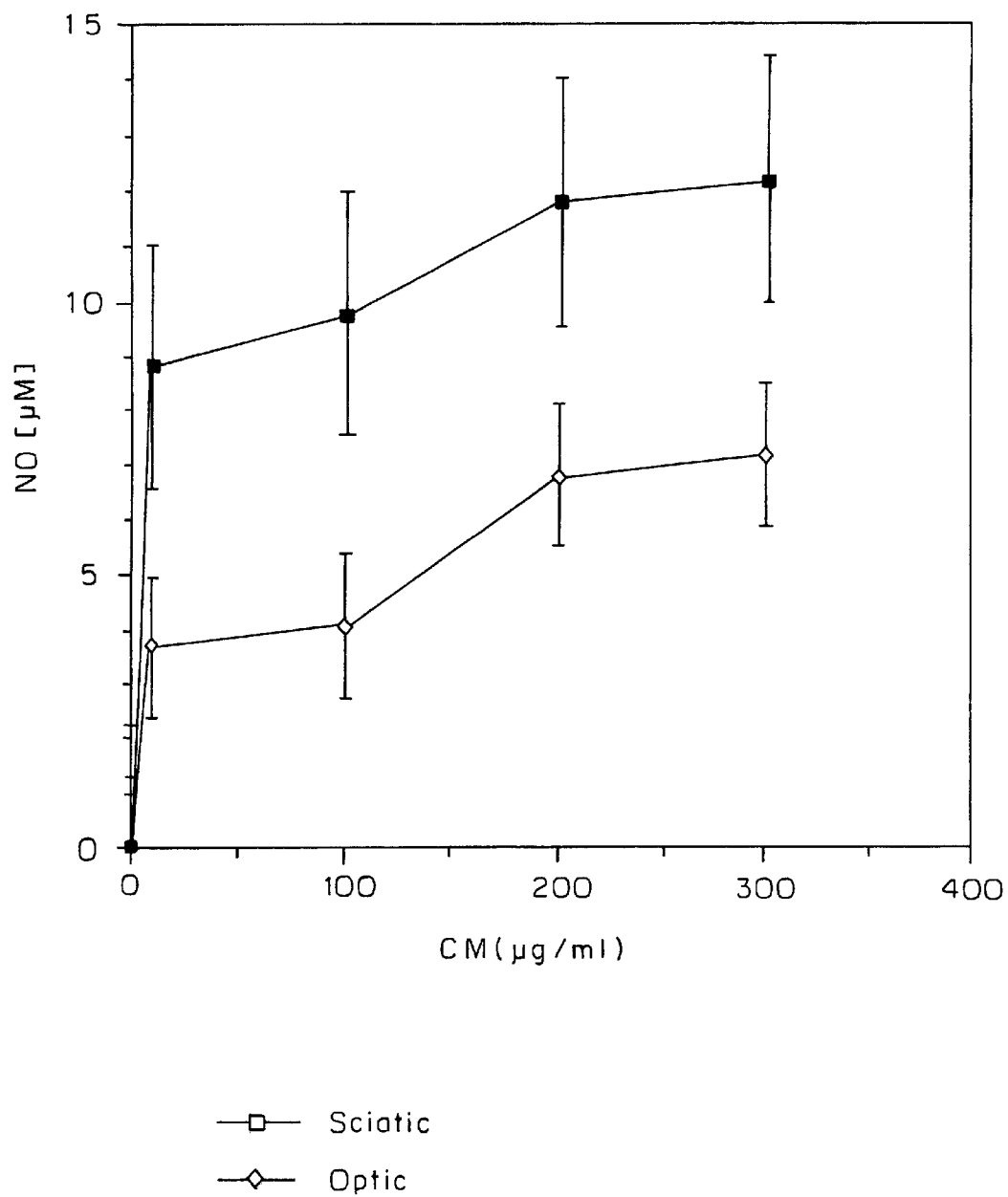

FIG. 13 illustrates nitric oxide production by rat monocytes cultured for 72 hours with medium conditioned by rat sciatic nerve or rat optic nerve. See text, Section 6, for experimental details. $10^6$ rat monocytes were cultured in 1 ml DCCM-1 medium with no further additions or with the addition of sciatic nerve-conditioned medium or optic nerve-conditioned medium at a total protein concentration of 10, 100, 200 or 300 µg/ml. After 72 hours, the media were collected and the levels of nitric oxide were measured.

Figure 14:
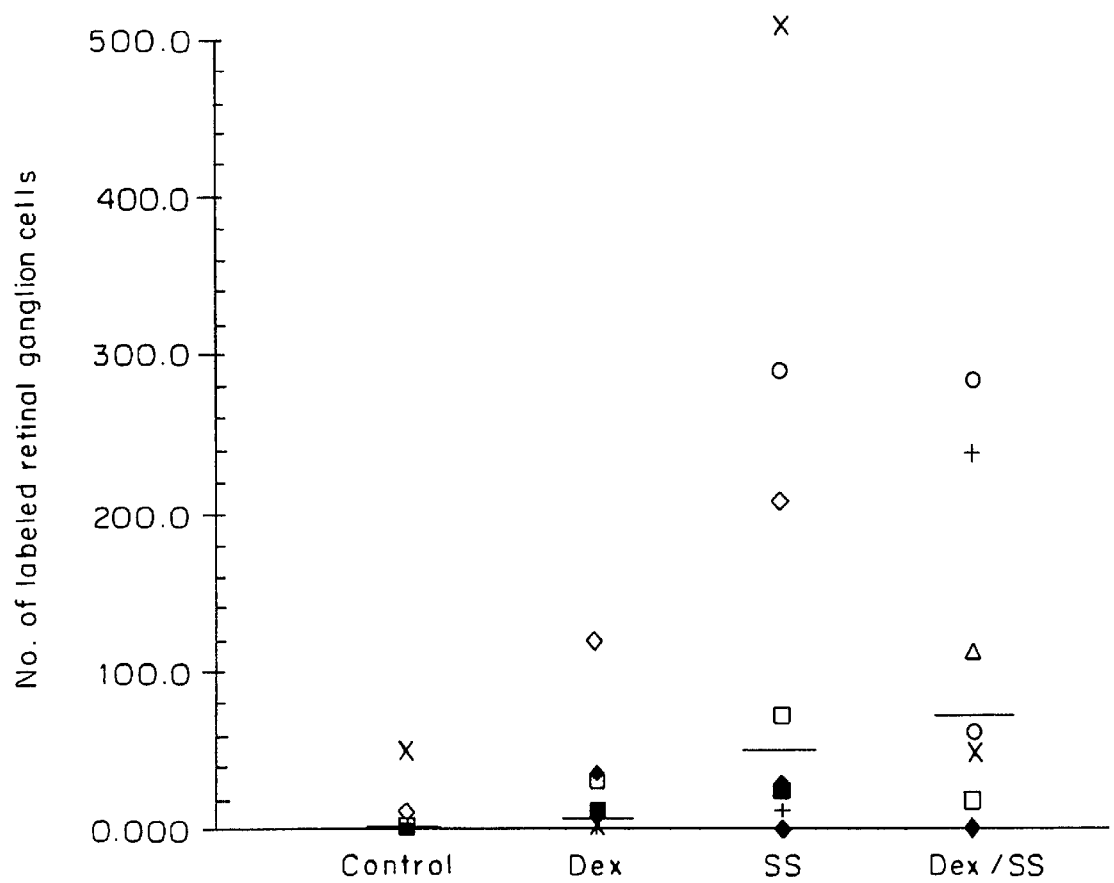

FIG. 14 illustrates axonal regeneration in transected optic nerves of rats following administration of optic nerve-stimulated monocytes combined with anti-inflammatory therapy. See text, Section 6, for experimental details. At the time of transection, 2 µl DCCM-1 medium were applied to the site of injury containing no cells or $5 \times 10^3$ sciatic nerve-stimulated rat monocytes. Concurrently, some of the rats received an intraperitoneal injection of 0.8 mg dexamethasone, producing the following treatment groups: no therapy (CONTROL), dexamethasone only (DEX), monocytes only (SS), and both dexamethasone and monocytes (DEX/SS).

Figure 15A:
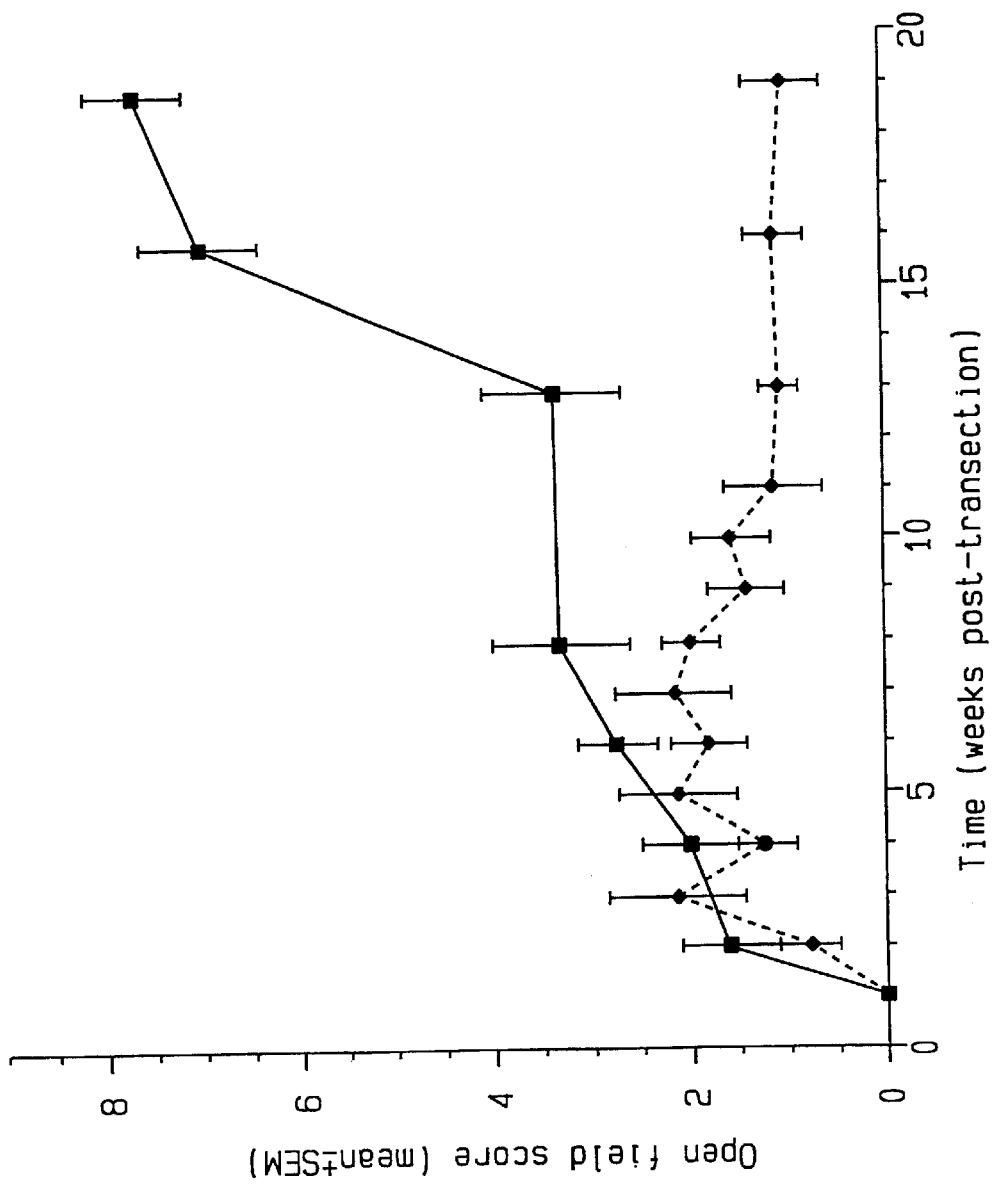
Figure 15B:
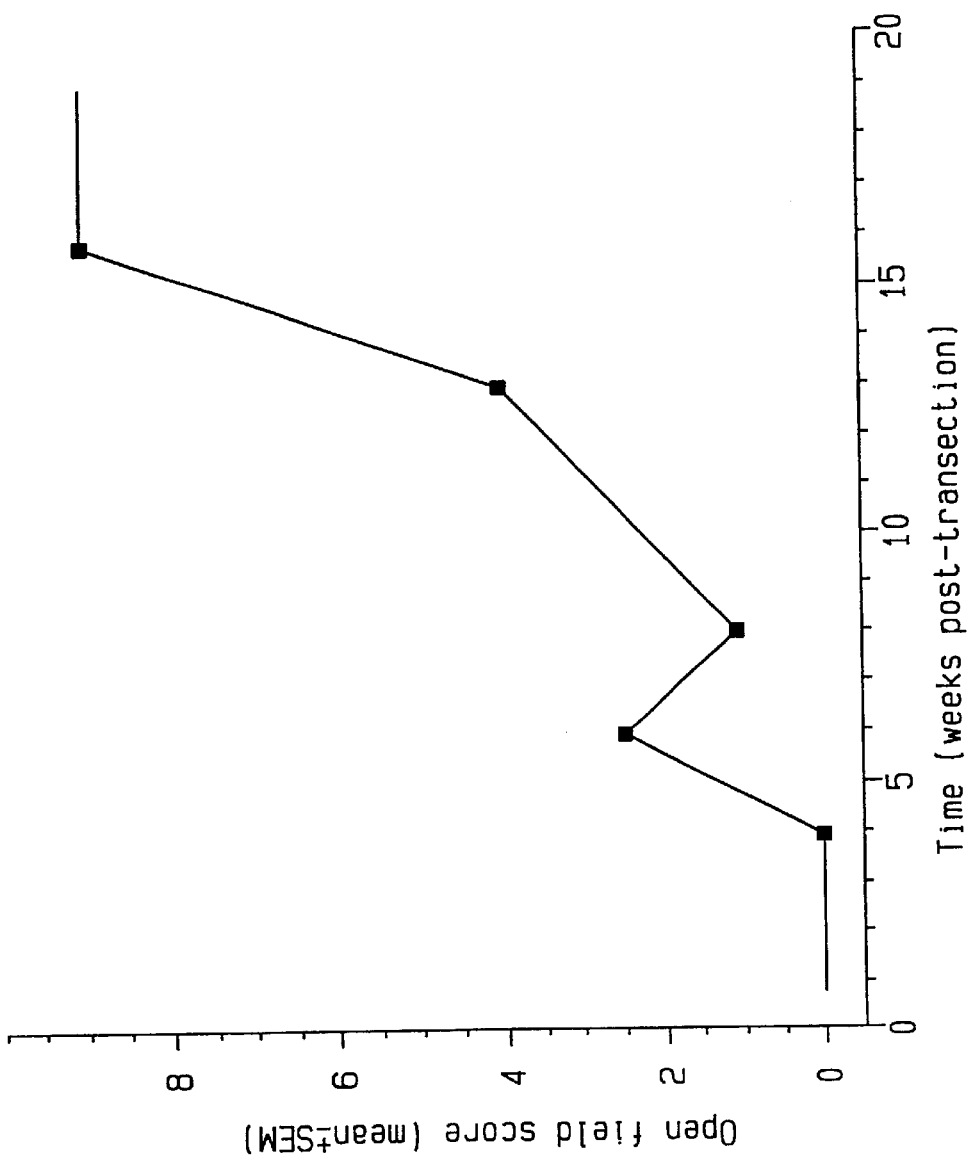
Figure 16A:
Figure 16A:
Figure 16B:
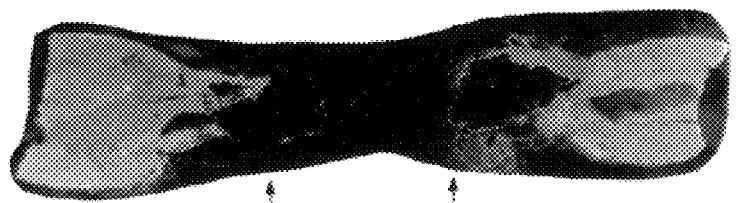
Figure 16B:
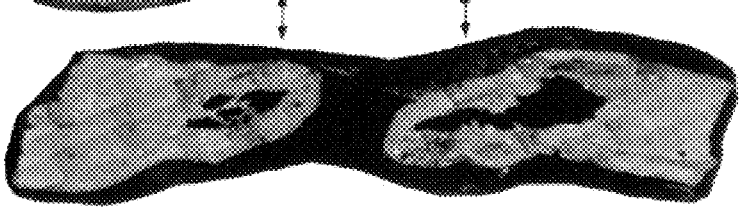
Figure 17A:
Figure 17B:
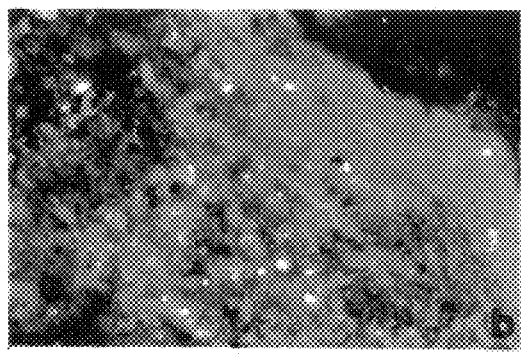
Figure 17C:
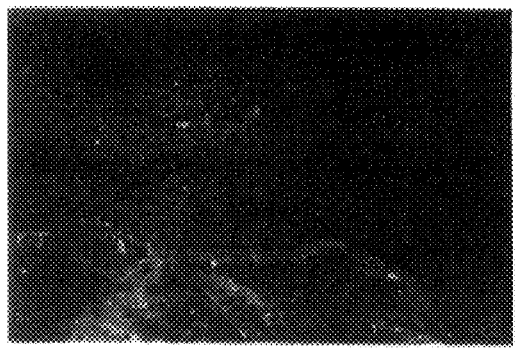
Figure 17D:
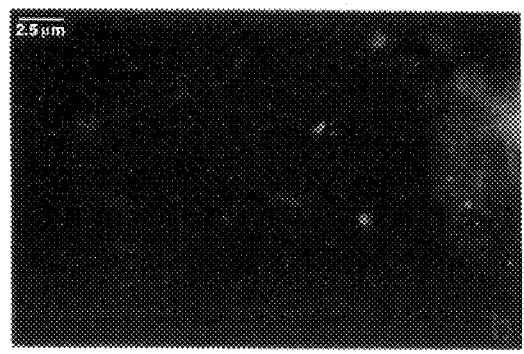

FIG. 15 illustrates recovery of voluntary motor function following administration of stimulated rat monocytes to rats that have undergone complete spinal cord transection. See text, Section 7, for experimental details. In FIG. 15A, the solid line presents the BBB locomotor scores (mean±SEM) for 8 out of 12 animals that showed motor recovery after spinal cord transection and treatment with stimulated monocytes, and the broken line presents the BBB locomotor scores of control animals following spinal cord transection. FIG. 15B shows serial BBB locomotor scores for an individual animal subjected to spinal cord transection and treated with $4 \times 10^5$ stimulated monocytes plus aFGF.

FIG. 16 presents low-power micrographs of transected spinal cord in rats treated with stimulated monocytes (A) or control medium (B), processed for immunohistochemical detection of GFAP (a) or neurofilament antigens (b). See text, Section 7, for experimental details. Each picture is a montage of approximately 100 frames, each photographed at 10× magnification.

FIG. 17 presents high-power micrographs of transected spinal cord in rats treated with stimulated monocytes (A) or control medium (B), processed for immunohistochemical detection of neurofilament antigens (a) or GAP-43 (b). See text, Section 7, for experimental details. Bar: 2.5 µm.

5. DETAILED DESCRIPTION OF THE INVENTION

5.1 MONONUCLEAR PHAGOCYTES

The present invention provides methods and compositions for use of allogeneic mononuclear phagocytes to promote axonal regeneration following injury or disease of the central nervous system (CNS). Allogeneic mononuclear phagocytes are introduced at or near the site of CNS injury or disease.

As used herein, the term "mononuclear phagocytes" is intended to comprise, without limitation, monocytes obtained from central or peripheral blood, macrophages obtained from any site, including any tissue or cavity, macrophages derived by culturing macrophage precursors obtained from bone marrow or blood, dendritic cells obtained from any site, including spleen, lymph node, skin and lymphatic fluid, and dendritic cells derived from culturing dendritic cell precursors obtained from bone marrow or blood.

Allogeneic mononuclear phagocytes can be obtained from the circulation or from any tissue in which they reside. Peripheral blood is an easily accessible ready source of allogeneic monocytes and is used as a source according to a preferred embodiment of the invention. Especially preferred is the use of autologous monocytes purified from the peripheral blood of a subject to whom the therapeutic preparation is intended to be administered.

Allogeneic mononuclear phagocytes from other sources are well known in the art and include, without limitation, macrophages obtained from serosal cavities such as the peritoneal or pleural cavity, alveolar macrophages, and macrophages associated with other tissues, (e.g. liver, spleen, thymus) where they may be known by various terms such as Kupffer cells (in the liver) and microglial cells (in the CNS). Allogeneic mononuclear phagocytes further include dendritic cells, which likewise may be known by various terms, such as Langerhans cells (in the skin), veiled cells (in lymphatic fluid) and interdigitating cells (in lymph nodes). Additionally mononuclear phagocytes can be derived by culture from allogeneic brain-derived mixed glial cells or from allogeneic precursor cells, which may be obtained from bone-marrow or blood. Preferably, the allogeneic mononuclear phagocytes are not microglia and are not derived by culture from brain-derived mixed glial cells.

In a preferred embodiment, cells other than mononuclear phagocytes are depleted from the cell population to be administered. Enrichment techniques are well known to those skilled in the art and include, without limitation, elutriation; centrifugation through material of suitable density, such as a Percoll gradient (Colotta et al., 1984, J. Immunol. 132:936–944); selective adhesion on suitable surfaces followed by removal at reduced temperature or at reduced concentrations of divalent cations (Rosen and Gordon, 1987, J. Exp. Med. 166:1685–1701), mechanical removal, or removal in the presence of lidocaine; and techniques for isolating dendritic cells from blood (O'Doherty et al., 1993, J. Exp. Med. 178:1067–1078), bone marrow (Inaba et al., 1992, J. Exp. Med. 176:1693–1702) and lymphoid tissue (Macatonia et al., J. Exp. Med. 169:1255–1264). Preferably, at least 50%, more preferably at least 70%, still more preferably at least 80%, and yet more preferably at least 90% of the cells are mononuclear phagocytes. Especially preferred is a substantially purified preparation of mononuclear phagocytes. e.g. a preparation in which at least 95% of the cells are mononuclear phagocytes.

Once the mononuclear phagocytes are obtained they may be used therapeutically at any desired time, according to the needs of the patient. The mononuclear phagocytes may, if desired, be cultured prior to administration in any suitable culture medium. Preferably, the mononuclear phagocytes are cultured in a vessel made from sterile material to which these cells show limited or no adherence. In a preferred embodiment, the mononuclear phagocytes are cultured in sterile Teflon bags prior to administration.

As used herein, "stimulated" mononuclear phagocytes are mononuclear phagocytes with an enhanced capacity to promote axonal regeneration. Preferably, the capacity of the mononuclear phagocytes to promote axonal regeneration is enhanced at least three-fold over non-stimulated mononuclear phagocytes, more preferably the capacity of the mononuclear phagocytes to promote axonal regeneration is enhanced at least 15-fold over non-stimulated mononuclear phagocytes. "Stimulatory" tissue, cells and biologically active agents are tissue, cells and biologically active agents that, when cultured together with mononuclear phagocytes, enhance the capacity of the mononuclear phagocytes to promote axonal regeneration.

In a preferred embodiment, stimulatory tissue, cells or at least one stimulatory biologically active agent is added to the culture in order to enhance the capacity of the mononuclear phagocytes to promote axonal regeneration. Preferably, one or more segments of a nerve, most preferably a peripheral nerve such as the sciatic nerve, are added to the culture. A xenogeneic nerve is suitable for this purpose or, more preferably, an allogeneic or autologous nerve. If desired, a human nerve can be obtained from any available human tissue, such as a human cadaver or a surgical specimen (e.g. an amputated limb). Alternatively other stimulatory tissue or cells are added to the culture. Dermis is suitable for this purpose and can be obtained, from a living donor or a cadaver, by punch biopsy, by surgical resection, or by any other suitable technique. Especially preferred is skin obtained by punch biopsy, particularly skin obtained from a patient to whom the stimulated mononuclear phagocytes are intended to be administered. Synovial tissue, tendon sheath and liver are also suitable for this purpose, as are other regenerating tissues. Additional stimulatory tissues and cells can be identified according to the assay described below. If desired, the stimulatory tissue or cells are homogenized before addition to the culture. As will be evident to those skilled in the art, the stimulatory tissue or cell homogenate can be preserved, e.g. by cryopreservation, before use.

In an alternative embodiment, at least one stimulatory biologically active agent is added to the culture in order to enhance the capacity of the mononuclear phagocytes to promote axonal regeneration. Transforming growth factor-beta (TGF-β), neurotrophic factor 3 (NT-3), nerve growth factor (NGF), brain-derived neurotrophic factor, β-interferon (IFN-β), γ-interferon (IFN-γ), tumor necrosis factor a (TNF-α), interleukin 2 (IL-2), interleukin 3 (IL-3), interleukin 4 (IL-4), interleukin 10 (IL-10), monocyte chemotactic and activating factor (MCAF), macrophage colony stimulating factor (M-CSF), granulocyte-macrophage colony stimulating factor (GM-CSF), colony stimulating factor 1 (CSF-1), lipid A, fMet-Leu-Phe (fMLP), muramyl dipeptide (MDP), the ionophore A23187, and vitamin D3 binding protein are suitable for this purpose either singly or in combination. Additional stimulatory biologically active agents (including additional stimulatory proteins and peptides) can be identified according to the assay described below.

A biologically active protein or peptide may be used in its native or recombinant form, at a concentration (for each protein or peptide) of 1 to 5000 ng/ml, more preferably 10 to 5000 ng/ml, still more preferably 100 to 2500 ng/ml, most preferably about 1000 ng/ml. In one embodiment, mononuclear phagocytes are stimulated by culturing them in medium to which IL-4 or IL-10 (and more preferably both IL-4 and IL-10) have been added.

Preferably, the mononuclear phagocytes are cultured together with stimulatory tissue, stimulatory cells, homogenate of stimulatory tissue or stimulatory cells, or at least one stimulatory biologically active agent for 24 hours. Shorter periods of culture, such as approximately 2 hours, are also effective, as are longer periods of culture, such as one or more weeks. In an alternative embodiment, stimulatory conditioned medium is prepared by incubating stimulatory tissue or cells, preferably one or more segments of a nerve, most preferably a peripheral nerve such as the sciatic nerve, in any medium that is suitable for culturing mononuclear phagocytes. After removal of the tissue or cells, mononuclear phagocytes are cultured in the stimulatory conditioned medium in order to enhance their capacity to promote axonal regeneration. After removal of the tissue or cells, the stimulatory conditioned medium can be stored and later used as desired for stimulating mononuclear phagocytes. Such stimulatory conditioned medium can be provided in the form of a commercial kit. Preferably, the stimulatory conditioned medium is preserved during storage, for instance by refrigeration, whether as a liquid or as frozen medium. Alternatively, the stimulatory conditioned medium is lyophilized.

In a preferred embodiment, the mononuclear phagocytes are exposed to a tyrosine kinase inhibitor, such as tyrphostine, before, during, or after stimulation, so as to reduce or eliminate undesired mononuclear phagocyte activities, such as secretion of TNF-α.

As will be evident to those skilled in the art, the mononuclear phagocytes can be preserved, e.g. by cryopreservation, either before or after culture.

Cryopreservation agents which can be used include but are not limited to dimethyl sulfoxide (DMSO) (Lovelock and Bishop, 1959, Nature 183:1394–1395; Ashwood-Smith 1961, Nature 190:1204–1205), glycerol, polyvinylpyrrolidone (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery, P. L. T., ed., Butterworth, London, p. 59), and DMSO combined with hydroxyethel starch and human serum albumin (Zaroulis and Leiderman, 1980, Cryobiology 17:311–317).

A controlled cooling rate is critical. Different cryoprotective agents (Rapatz et al., 1968, Cryobiology 5(1):18–25) and different cell types have different optimal cooling rates. See, e.q., Rowe and Rinfret, 1962, Blood 20:636; Rowe, 1966, Cryobiology 3(1):12–18; Lewis et al., 1967, Transfusion 7(1):17–32; and Mazur, 1970, Science 168:939–949 for effects of cooling velocity on survival of marrow-stem cells and on their transplantation potential. The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In one embodiment, samples can be cryogenically stored in mechanical freezers, such as freezers that maintain a temperature of about −80° C. or about −20° C. In a preferred embodiment, samples can be cryogenically stored in liquid nitrogen (−196° C.) or its vapor. Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Considerations and procedures for the manipulation, cryopreservation, and long term storage of hematopoietic stem cells, particularly from bone marrow or peripheral blood, are largely applicable to the mononuclear phagocytes of the invention. Such a discussion can be found, for example, in the following references, incorporated by reference herein: Gorin, 1986, Clinics in Haematology 15(1):19–48; Bone-Marrow Conservation, Culture and Transplantation, Proceedings of a Panel, Moscow, Jul. 22–26, 1968, International Atomic Energy Agency, Vienna, pp. 107–186.

Other methods of cryopreservation of viable cells, or modifications thereof, are available and envisioned for use, e.g., cold metal-mirror techniques. See Livesey and Linner, 1987, Nature 327:255; Linner et al., 1986, J. Histochem. Cytochem. 34(9):1123–1135; see also U.S. Pat. No. 4,199,022 by Senken et al., U.S. Pat. No. 3,753,357 by Schwartz, U.S. Pat. No. 4,559,298 by Fahy.

Frozen cells are preferably thawed quickly (e.g., in a water bath maintained at 37–41° C.) and chilled immediately upon thawing. It may be desirable to treat the cells in order to prevent cellular clumping upon thawing. To prevent clumping, various procedures can be used, including but not limited to the addition before and/or after freezing of DNAse (Spitzer et al., 1980, Cancer 45:3075–3085), low molecular weight dextran and citrate, hydroxyethyl starch (Stiff et al., 1983, Cryobiology 20:17–24), or acid citrate dextrose (Zaroulis and Leiderman, 1980, Cryobiology 17:311–317), etc.

The cryoprotective agent, if toxic in humans, should be removed prior to therapeutic use of the thawed mononuclear phagocytes. One way in which to remove the cryoprotective agent is by dilution to an insignificant concentration.

Once frozen mononuclear phagocytes have been thawed and recovered, they are used to promote axonal regeneration as described herein with respect to non-frozen mononuclear phagocytes.

5.2 METHODS OF USE

In one embodiment of the present invention, the mononuclear phagocytes are suspended in a sterile pharmaceutically acceptable carrier and administered into the CNS of a mammal, including a human subject, at or near a site of injury or disease. In a preferred embodiment, the pharmaceutically acceptable carrier is PBS, a culture medium, or any pharmaceutically acceptable fluid in which the mononuclear phagocytes are suspended. However, alternative pharmaceutically acceptable carriers will readily be apparent to those skilled in the art.

If desired, treatment with mononuclear phagocytes may optionally be combined with local or systemic anti-inflammatory therapy, for instance administration of (a) a steroid such dexamethasone or methylprednisolone, (b) a non-steroidal anti-inflammatory agent (NSAID), such as aspirin, indomethacin, ibuprofen, fenoprofen, ketoprofen or naproxen, or (c) an anti-inflammatory peptide, such as Thr-Lys-Pro (TKP). The present invention encompasses the optional use of an anti-inflammatory agent at any dose that is effective in the subject to be treated. Such effective doses are well known to those skilled in the art and include, for example, standard-dose therapy, such as systemic methylprednisolone 100 mg daily for a human adult, and high-dose therapy, such as systemic methylprednisolone 1000 mg daily for a human adult.

In accordance with the present invention, treatment with mononuclear phagocytes may optionally be combined with concurrent administration to the CNS of one or more adjuvant factors. Adjuvant factors suitable for this purpose include acidic fibroblast growth factor (aFGF); transforming growth factor-beta (TGF-β); interleukin 6 (IL-6); neurotrophic factors, e.g. nerve growth factor (NGF), neurotrophic factor 3 (NT-3), neurotrophic factor 4 (NT-4), neurotrophic factor 5 (NT-5), and brain-derived neurotrophic factor (BDNF); and the neuronal cell adhesion molecule known as L1 (L1CAM) see Kallunki et al., 1997, J. Cell Biol. 138: 1343–1354. Acidic fibroblast growth factor (aFGF) is especially preferred. Each adjuvant factor can be administered at a dose of 6 to 10 ng/kg, either as a single dose or in repeated doses, e.g. at weekly intervals. In one embodiment, one or more adjuvant factors are administered into the CNS at or near a site of disease or injury that is treated with mononuclear phagocytes, either together with, or shortly before or after administration of the mononuclear phagocytes. Alternatively, one or more adjuvant factors are administered regionally, such as by intraventricular administration for treatment of the brain, by intrathecal administration for treatment of the spinal cord, or by intraocular administration for treatment of the retina or optic nerve. Both native and recombinant adjuvant factors can be used. The present invention further encompasses combined treatment with (a) mononuclear phagocytes, (b) steroidal or non-steroidal anti-inflammatory therapy, and (c) one or more adjuvant factors.

In a preferred embodiment, the mononuclear phagocytes are administered immediately following CNS injury and are introduced at the site of CNS injury, for example with a glass micropipette. However, the present invention encompasses administration of mononuclear phagocytes at any time (e.g. within a week, a fortnight, a month, 2 months, 3 months or 6 months) after the CNS sustains injury or disease, and encompasses introduction of the mononuclear phagocytes at or near a site of CNS injury or disease by any neurosurgically suitable technique.

The compositions and methods of the present invention are useful for treating any injury or disease of the CNS that results in or is accompanied by axonal damage. The injury or disease may be situated in any portion of the CNS, including the brain, spinal cord, or optic nerve. One example of such injury or disease is trauma, including coup or countercoup injury, penetrating trauma, and trauma sustained during a neurosurgical operation or other procedure. Another example of such injury or disease is stroke, including hemorrhagic stroke and ischemic stroke. Yet another example of such injury or disease is optic nerve injury accompanying optic neuropathy or glaucoma. Still further examples of CNS injury or disease will be evident to those skilled in the art from this description and are encompassed by the present invention. The compositions and methods of the present invention are useful for treating CNS injury or disease that results in axonal damage whether or not the subject also suffers from other disease of the central or peripheral nervous system, such as neurological disease of genetic, metabolic, toxic, nutritional, infective or autoimmune origin.

The optimal dose of mononuclear phagocytes is proportional to the number of nerve fibers affected by CNS injury or disease at the site being treated. In a preferred embodiment, the dose ranges from about $2.5 \times 10^3$ to about $10^5$ mononuclear phagocytes for treating a lesion affecting about $10^5$ nerve fibers, such as a complete transection of a rat optic nerve, and ranges from about $2.5 \times 10^4$ to about $10^6$ mononuclear phagocytes for treating a lesion affecting about $10^6$ nerve fibers, such as a complete transection of a human optic nerve. More preferably, the dose ranges from about $10^4$ to about $10^5$ mononuclear phagocytes for treating a lesion affecting about $10^5$ nerve fibers and ranges from about $10^5$ to about $10^6$ mononuclear phagocytes for treating a lesion affecting about $10^6$ nerve fibers. As will be evident to those of skill in the art, the dose of mononuclear phagocytes can be scaled up or down in proportion to the number of nerve fibers affected at the lesion or site of injury being treated.

5.3 ASSAY FOR STIMULATORY TISSUES, CELLS AND BIOLOGICALLY ACTIVE AGENTS

The present invention provides an assay for identifying stimulatory tissues and cells and stimulatory biologically active agents. Mononuclear phagocytes are cultured together with the tissue or cells to be tested, in medium conditioned by the tissue or cells to be tested, or in medium to which the biologically active agent or agents to be tested have been added at various concentrations. Thereafter, the mononuclear phagocytes are assayed for phagocytic activity, or nitric oxide production. Mononuclear phagocytes with increased phagocytic activity or increased production of nitric oxide have an enhanced capacity to promote axonal regeneration. In a preferred embodiment, both phagocytic activity and nitric oxide production are measured, and mononuclear phagocyte stimulation is detected by observing an increase in either of these activities, more preferably in both of these activities.

Preferably, the phagocytic capacity of the mononuclear phagocytes is increased by at least 10 percent, more preferably by at least 25 percent, still more preferably by at least 50 percent. Preferably, the nitric oxide production of the mononuclear phagocytes is increased by at least 50 percent, more preferably by at least 100 percent, and still more preferably by at least 200 percent.

In one embodiment, phagocytic activity is measured by contacting the mononuclear phagocytes with labeled particles and subsequently determining the amount of label associated with the cells. A wide variety of particles can be used for this purpose, including without limitation latex or polystyrene beads and naturally occurring cells, such as red blood cells, yeast and bacteria. Optionally, the particles can be opsonized, for instance with immunoglobulin or complement. The particles can be labeled with any suitable marker, including without limitation a fluorescent marker (such as fluorescein or rhodamine), a radioactive marker (such as a radioactive isotope of iodine, carbon or hydrogen), and an enzyme. Alternatively, the assay can be performed with unlabeled particles (e.g. red blood cells or yeast); the unlabeled particles are detected by any suitable method, such as microscopically, with or without staining. In a preferred embodiment, the mononuclear phagocytes are first contacted with fluorescent polystyrene beads; cell-associated fluorescence is subsequently measured by flow cytometry.

In one embodiment, nitric oxide production is measured by the Griess-reagent assay as described in Hibbs et al., 1987, Science 235:473–476, which is incorporated herein by reference. However, other assays for nitric oxide production may be used, as are known to those of skill in the art. See, e.g., Packer (ed.), 1996, Methods in Enzymology 268:58–247, which is incorporated herein by reference.

The assay of the present invention also provides a means of determining the period of culture required in order to stimulate the mononuclear phagocytes. Mononuclear phagocytes are cultured for various periods with stimulatory tissue or cells, in medium conditioned by stimulatory tissue or cells, or in medium to which at least one stimulatory biologically active agent has been added. Thereafter, the phagocytic activity or nitric oxide production of the mononuclear phagocytes, or both these properties, are measured. A period of culture sufficient to increase the phagocytic activity of the mononuclear phagocytes by at least 10 percent, preferably by at least 25 percent, more preferably by at least 50 percent, or sufficient to increase the nitric oxide production of the mononuclear phagocytes by at least 50 percent, preferably by at least 100 percent, more preferably by at least 200 percent, is sufficient to stimulate their capacity to enhance axonal regeneration.

The following examples are presented for purposes of illustration only and are not intended to limit the scope of the invention in any way.

6. EXAMPLE: USE OF MONOCYTES TO PROMOTE AXONAL REGENERATION IN TRANSECTED OPTIC NERVE 6.1 MATERIALS AND METHODS 6.1.1 Isolation and Culture of Monocytes Peripheral blood was pooled from adult Sprague-Dawley (SPD) rats. Monocytes were isolated by fractionation on a one-step Percoll gradient as previously described. F. Colotta et al., 1984, J. Immunol. 132:936–944. The monocyte-enriched fraction was recovered from the Percoll interface, washed once with PBS to remove traces of Percoll, and resuspended at $1 \times 10^6$ cells/ml in DCCM-1 medium (Beit Ha'emek Ltd., Kibbutz Beit Ha'emek, Israel). The cells were cultured in Teflon bags at 37° C. as previously described, Andreesen et al., 1983, J. Immunolog. Meth. 56:295–304, with 5% $CO_2$, as is conventional in the art. Usually, each bag received 10 ml containing $1 \times 10^7$ cells. For measurement of phagocytic activity or nitric oxide production, monocytes from SPD or Wistar rats were used, and were cultured in polypropylene tubes or in Teflon bags.

6.1.2 Stimulation of Monocytes

Non-stimulated monocytes (NS) were prepared by culturing isolated monocytes in a Teflon bag or polypropylene tubes, as described above, for 2–24 hours. Sciatic nerve-stimulated monocytes (SS) were prepared by culturing monocytes in a Teflon bag or polypropylene tubes for 2–24 hours together with at least one segment of a rat sciatic nerve. Optic nerve-stimulated monocytes (OS) were prepared by culturing monocytes in a Teflon bag or polypropylene tubes for 2–24 hours together with at least one segment of a rat optic nerve. Each nerve segment was 1.0–1.5 cm long in experiments 6.2.1 and 6.2.2, and was 0.5–1.0 cm long in experiments 6.2.3 to 6.2.9; a constant ratio of 1 nerve segment to $5 \times 10^6$ cultured monocytes was used, except where otherwise noted.

After 2–24 hours in culture, monocytes were centrifuged for 3 minutes at 1000×g, washed once with phosphate buffered saline (PBS), and resuspended in DCCM-1 medium at $1.25 \times 10^6$–$5 \times 10^6$ cells/ml. The monocytes were 95% pure as determined by morphology and by immunocytochemistry with the monoclonal antibody ED1 (Serotec, Oxford, England) as described. Hirschberg et al., 1994, J. Neuroimmunol. 50:9–16

Skin was also used to stimulate monocytes. In some experiments, $10^6$ rat monocytes were cultured with a 1 cm×1 cm square of skin obtained from germ-free rats by punch biopsy. In other experiments, rat skin was cultured in protein-free medium to produce skin-conditioned medium containing skin-derived proteins; $10^6$ rat monocytes were then cultured with skin-conditioned medium containing 200 µg of protein.

6.1.3 Optic Nerve Transection

Anesthetized adult SPD rats, 8–9 weeks old, average mass 300 grams, were subjected to optic nerve transection as described. Eitan et al., 1994, Science 264:1764–1768. The left optic nerve was exposed through a small opening in the meninges. A curved glass dissector with a 200 µm tip and a smooth blunt edge was moved across the nerve to create a complete transection 2–3 mm distal to the optic globe, taking care not to damage the peripheral blood vessels. As used herein, the term "distal" means away from the optic globe and towards the brain. Shortly after transection, 2 µl of medium containing cultured monocytes or 2 µl of medium alone were introduced at the site of injury by means of a curved glass micropipette with a 25 µm lumen. The meningeal opening was made about 200 µm from the site of transection, in order to minimize leakage of cells from the site of application. In some experiments, dexamethasone (0.8 mg/rat) was administered by intraperitoneal injection to some of the rats shortly after transection.

6.1.4 Assays for Axonal Regeneration

6.1.4.1 Retrograde Labeling of Axons

Seven to eight weeks following transection, the lipophilic neurotracer dye, 4-(4-(didecylamino)styryl)-N-methylpyridinium iodide (4Di-10ASP) (Molecular Probes, Eugene, Oreg., USA) was applied to the injured optic nerve, 2 mm distal to the site of injury. One week after application of the dye, the retina was removed, prepared as a flattened whole mount in 4% paraformaldehyde solution, and examined by fluorescence microscopy to detect and count the number of labeled retinal ganglion cells (RGCs) in the entire retina. Only axons that had regrown past the site of injury to the site at which dye was applied could take up the dye and transport it retrogradely to the retinal ganglion cells.

When applied to rat optic nerves that have not previously been transected, this procedure labels an average of 21,623 RGCs per retina. The results for optic nerves that were subjected to transection are expressed as a percentage of this standard, to control for the efficiency of the 4Di-10ASP labeling technique.

6.1.4.2 Anterograde Labeling of Axons

Seven to eight weeks following transection, a fresh incision was made in the previously transected optic nerve 1 mm proximal to the site of transection. As used herein, "proximal" means towards the optic globe and away from the brain. Horseradish peroxidase (HRP) (type VI-A, Sigma, Tel Aviv, Israel) was introduced through the incision by means of a sterile swab soaked in a 50% (w/v) solution of HRP in PBS. Eight to twelve hours after application of the HRP, the rats were perfused through the carotid artery with PBS followed by 4% paraformaldehyde in PBS as a fixative. The optic nerves were excised, 50 µm longitudinal cryosections were taken and processed for visualization of HRP activity using diaminobenzidine and cobalt intensification as described. Lavie et al., 1992, Brain Res. 575:1–5.

6.1.5 Assay of Phagocytic Activity

Monocytes from SPD or Wistar rats were suspended in DCCM-1 medium ($2.5 \times 10^5$ or $5 \times 10^5$ cells in 1 ml) and were cultured without further additions or together with the indicated number of syngeneic rat sciatic or optic nerve segments or with the addition of medium conditioned by syngeneic rat optic nerve at the indicated concentrations of total protein. See Section 4 for details. To assay phagocytic activity, a working solution of fluorescent noncarboxylated microspheres ("FLUORESBRITE"™, Polysciences, Warrington, Pa., USA, Catalog. No. 17152) was prepared by diluting 1 drop of a stock solution in 10 ml DCCM-1 medium and adding this working solution to the monocyte suspension at a further dilution of 1:100, after removing the nerve segments. After three hours at 37° C., the cells were washed once with DCCM-1 medium or with phosphate-buffered saline, and cell-associated fluorescence was measured by flow cytometry (FACS). In some experiments, 1 ml ice-cold PBS was added prior to the washing step, to halt phagocytosis.

6.1.6 Assay of Nitric Oxide Production

Monocytes from SPD or Wistar rats were suspended in DCCM-1 medium ($10^6$ cells in 1 ml) and were cultured without further additions or with the indicated number of syngeneic rat sciatic or optic nerve segments or with the addition of medium conditioned by syngeneic rat sciatic or optic nerve at the indicated concentrations of total protein. See Section 4 for details. After the indicated time in culture, the nerve segments (if any) were removed, the samples were centrifuged, and the supernatants were collected. To assay nitric oxide production, 100 µl aliquots of supernatant were incubated with 100 µl of Griess reagent (1% sulfanilamide, 10% N-(1-naphthyl)-ethylene diamine hydrochloride in 2.5% $H_3PO_4$) at room temperature for 10 minutes. Colorimetry was performed at 550 nm with an ELISA reader and the amount of nitric oxide calculated according to a reference curve using sodium nitrite (Sigma, Israel) as standard. The reaction medium (DCCM-1) was used as a blank. In control experiments, optic and sciatic nerve segments were found to produce negligible amounts of nitric oxide.

6.2 RESULTS

6.2.1 Promotion of Axonal Regeneration by Stimulated and Non-Stimulated Monocytes Rats were subjected to optic nerve transection and treated at the time of injury with control medium or with $2.5 \times 10^3$–$1 \times 10^5$ non-stimulated (NS) monocytes, $2.5 \times 10^3$–$1 \times 10^5$ sciatic nerve-stimulated (SS) monocytes, or $2.5 \times 10^3$–$1 \times 10^5$ optic nerve-stimulated (OS) monocytes.

The number of labeled retinal ganglion cells (RGCS) in rats from each treatment group is shown in FIG. 1 as a percentage of RGCs labeled in normal optic nerves. Rats receiving no cells showed almost no labeling of RGCs. Rats receiving NS monocytes showed labeling of modest numbers of RGCs, while treatment with OS monocytes resulted in labeling of greater numbers of RGCs. In rats receiving SS monocytes, the median number of labeled RGCs was over 5-fold higher than in the rats treated with OS monocytes, and was about 15-fold higher than in the rats treated with NS monocytes.

6.2.2 Axonal Regeneration After Treatment with Various Doses of Sciatic Nerve- or Optic Nerve-Stimulated Monocytes To study regeneration as a function of the dose of monocytes administered, rats were subjected to optic nerve transection and treated at the time of injury with OS monocytes or SS monocytes at a total dose of $2.5 \times 10^3$; $5 \times 10^3$; $1 \times 10^4$; or $1 \times 10^5$ cells.

The average number of labeled retinal RGCs in each treatment group is shown in FIG. 2 as a percentage of RGCs labeled in normal optic nerves. RGC labeling was highest after treatment with $5 \times 10^3$ SS monocytes. Higher or lower doses of SS monocytes promoted axonal regeneration but were less effective. Treatment with OS monocytes similarly promoted axonal regeneration, though less effectively. The peak effect, with both Os and SS monocytes, occurred at a dose of 5×1 monocytes; at higher or lower doses the beneficial effect on axonal regeneration was less marked.

Representative fluorescence micrographs of labeled RGCs in retinas after treatment with SS monocytes or control medium are shown in FIG. 3. The absence of labeled RGCs following treatment with control medium indicates that transection was complete and that the labeled RGCs represent regenerating axons that traversed the site of transection and not merely fibers that escaped the experimental injury.

The photomicrographs in FIG. 4 further verify that regrowth has occurred. In nerves treated with control medium (E) no labeled fibers could be seen distal to the site of HRP application. In nerves treated with SS monocytes (A–D) labeled fibers were seen emerging from the proximal part of the nerve, crossing the site of transection (ST) and extending distally. Structures resembling growth cones (gc) were observed at the tips of these labeled fibers.

6.2.3 Axonal Regeneration After Treatment with Monocytes Stimulated with Rat Sciatic Nerve Segments for Various Intervals To study the capacity of monocytes to promote axonal regeneration after stimulation for various intervals with sciatic nerve segments, rats were subjected to optic nerve injury and treated at the time of injury with $5 \times 10^3$ monocytes cultured with rat sciatic nerve segments for two hours (2h), twelve hours (12h) or seventeen hours (17h). The number of labeled RGCs in individual rats from each treatment group is shown in FIG. 5 as a percentage of RGCs labeled in normal optic nerves. Monocytes showed an enhanced capacity to promote axonal regeneration after culture with sciatic nerve segments for each interval tested.

6.2.4 Axonal Regeneration after Treatment with Monocytes Stimulated with Rat or Mouse Sciatic Segments To compare the ability of sciatic nerve segments derived from rat and mouse to stimulate the capacity of monocytes to promote axonal regeneration, rats were subjected to optic nerve transection and treated at the time of injury with $5 \times 10^3$ rat monocytes cultured for 24 hours either with 1–8 segments of rat sciatic nerve (RAT) or with 2–16 segments of mouse sciatic nerve (MOUSE). The number of labeled RGCs in individual rats from each treatment group is shown in FIG. 6 as a percentage of RGCs labeled in normal optic nerves. Both rat and mouse sciatic nerve stimulated the capacity of monocytes to promote axonal regeneration.

6.2.5 Phagocytic Activity of Monocytes Following Culture with segments of Rat Sciatic Nerve Rat monocytes were suspended at $2.5 \times 10^5$ cells in 1 ml DCCM-1 medium and were cultured for 2–24 hours without further additions (CONTROL), with 1 segment of rat sciatic nerve (1SS), with 2 segments of rat sciatic nerve (2SS), or with 4 segments of rat sciatic nerve (4SS).

The phagocytic activity of the 2SS and 4SS preparations after 2 hours in culture is shown in FIG. 7 relative to the phagocytic activity of CONTROL monocytes. After culture for 2 hours with two segments of sciatic nerve, the monocytes showed increased phagocytic activity; after culture for 2 hours with four segments of sciatic nerve, the monocytes showed a greater increase in phagocytic activity.

The phagocytic activity of the 1SS and 4SS preparations after 24 hours in culture is shown in FIG. 8 relative to the phagocytic activity of CONTROL monocytes. After culture for 24 hours with one segment of sciatic nerve, the monocytes showed increased phagocytic activity; after culture for 24 hours with four segments of sciatic nerve, the increase in phagocytic activity was even greater. The 4SS preparation showed a greater increase in phagocytic activity after 24 hours than after 2 hours.

Addition of sciatic nerve-conditioned medium to the monocyte culture likewise increased the phagocytic activity of the monocytes (data not shown).

6.2.6 Phagocytic Activity of Monocytes Following Culture with Segments of Rat Optic Nerve Rat monocytes were suspended at $2.5 \times 10^5$ cells in 1 ml DCCM-1 medium and were cultured for 2–24 hours without further additions (CONTROL) or with 4 segments of rat optic nerve (4OS). The phagocytic activity of the 4OS preparations after 2 hours in culture is shown in FIG. 9 relative to the phagocytic activity of CONTROL monocytes. After culture for 2 hours with four segments of optic nerve, the monocytes showed a decrease in phagocytic activity.

The phagocytic activity of the 4OS preparations after 24 hours in culture is shown in FIG. 10 relative to the phagocytic activity of CONTROL monocytes. After culture for 24 hours with four segments of optic nerve, the monocytes showed a decrease in phagocytic activity similar to that seen after 2 hours.

6.2.7 Phagocytic Activity of Monocytes Following Culture with Sciatic Nerve Segments in the Presence of Optic Nerve-Conditioned Medium Optic nerve conditioned medium was prepared by culturing 10 segments of rat optic nerve for 2 hours in 1 ml DCCM-1 medium. While fresh DCCM-1 medium is protein-free, the optic nerve conditioned medium contained protein. Rat monocytes were suspended at $2.5 \times 10^5$ cells in 1 ml DCCM-1 medium and were cultured for 24 hours with 1–6 segments of rat sciatic nerve without further additions (0) or with optic nerve conditioned medium at a total protein concentration of 10 $\mu$g/ml (10), 1 $\mu$g/ml (1) or 0.1 $\mu$g/ml (0.1).

FIG. 11 presents the phagocytic activity of monocytes cultured with sciatic nerve in the presence of optic nerve conditioned medium relative to the phagocytic activity of monocytes cultured with sciatic nerve in the absence of optic nerve conditioned medium. Addition of optic nerve conditioned medium attenuated the enhancement in phagocytic activity caused by culture with sciatic nerve. This attenuation was most marked in the preparation that received 0.1 $\mu$g/ml optic nerve conditioned medium. Similar results (not shown) were obtained when optic nerve segments were cultured in DCCM-1 medium for 8 hours and the resulting supernatants were dialyzed overnight at 4° C. against PBS and subsequently stored at −20° C. or −70° C.

6.2.8 Nitric Oxide Production of Monocytes Cultured with Sciatic Nerve, Optic Nerve, or Conditioned Medium Rat monocytes were suspended at $10^6$ cells in 1 ml DCCM-1 medium and were cultured for 24–96 hours without further additions (CONTROL), with 1 segment of rat sciatic nerve (1SS), or with 4 segments of rat optic nerve (4OS). The nitric oxide production of these preparations is shown in FIG. 12. Monocytes cultured with sciatic nerve showed significantly increased production of nitric oxide, whereas optic nerve had no significant effect.

FIG. 13 illustrates nitric oxide production of monocytes cultured for 72 hours with medium conditioned by rat sciatic nerve or rat optic nerve. Sciatic nerve-conditioned medium produced a statistically significant increase in nitric oxide production, whereas optic nerve-conditioned medium had no statistically significant effect. This result demonstrates that stimulation of mononuclear phagocytes by sciatic nerve is mediated by one or more soluble factors.

6.2.9 Axonal Regeneration after Treatment with Sciatic Nerve-Stimulated Monocytes Combined with Anti-Inflammatory Therapy To study whether anti-inflammatory therapy prevents monocyte-mediated axonal regeneration, rats were subjected to optic nerve transection. Control medium or sciatic nerve-stimulated monocytes were administered at the transection site shortly after injury, either without additional therapy or together with intraperitoneal administration of dexamethasone. Eight weeks later, axonal regeneration was measured by retrograde labeling. As shown in FIG. 14, rats receiving no therapy (CONTROL) or dexamethasone only (DEX) shown negligible regrowth, whereas sciatic nerve-stimulated monocytes promoted axonal regeneration, whether given alone (SS) or concurrently with intraperitoneal dexamethasone (DEX/SS).

6.3 DISCUSSION

These examples demonstrate that monocytes administered at a site of CNS injury promoted axonal regeneration. All monocytes tested were effective at promoting axonal regeneration. However, monocytes were stimulated (i.e., showed an enhanced capacity to promote axonal regeneration) by culture with a nerve segment, especially with a segment of a peripheral nerve, e.g. sciatic nerve from rat or mouse. This stimulation was evident after all periods of culture tested, i.e. from 2–24 hours. For treating a total transection of a rat optic nerve, which contains about $10^5$ nerve fibers, optimal results were obtained by administering about $5 \times 10^3$ monocytes. However, every dose tested showed a beneficial effect on axonal regeneration.

These examples also demonstrate that monocytes show increased phagocytic activity and increased nitric oxide production after culture with one or more segments of sciatic nerve or in sciatic nerve-conditioned medium. Thus, measurement of phagocytic activity, nitric oxide production or both these properties provides a rapid and efficient method of screening tissues and cells for their capacity to stimulate monocytes to promote axonal regeneration.

7. EXAMPLE: USE OF MONOCYTES TO PROMOTE AXONAL REGENERATION IN TRANSECTED SPINAL CORD

7.1 MATERIALS AND METHODS

7.1.1 Isolation and Stimulation of Monocytes

Peripheral blood from adult Sprague-Dawley (SPD) rats was drawn into 10 ml syringes coated with heparin (5000 u/ml, Calbiochem, La Jolla, Calif.), diluted with an equal volume of PBS, and subjected to fractionation on a one-step gradient of Percoll (1.077 g/ml, Pharmacia, Sweden) by centrifugation at 291×g for 25 min at 30° C. See Colotta et al., 1984, J. Immunol. 132: 936–944. The monocyte-enriched fraction was recovered from the Percoll interface, washed once with PBS to remove traces of Percoll, and resuspended at $1 \times 10^6$ cells/ml in DCCM-1 medium (Beit Ha'emek Ltd., Kibbutz Beit Ha'emek, Israel). The cells were incubated in polypropylene tubes or Teflon bags at 37° C., 5% $CO_2$, with freshly excised segments of rat sciatic nerve (0.5 to 1.0 cm long) for 2 to 24 hours ($0.4–5.0 \times 10^6$ cells/nerve segment).

7.1.2 Spinal Cord Transection

Male Sprague-Dawley rats (Hebrew University, Jerusalem, Israel), 200–300 g, were anesthetized with ketamine 40 mg/kg and xyline 100 mg/kg and incised dorsally to expose the T8–T9 vertebrae. The muscular insertions on the posterior and transverse vertebral processes were dissected and cut with a monopolar electrocautery device. T8 laminectomy was performed with a bone rongeur, without contusive injury to the underlying spinal cord. The spinal cord was transected with microscissors, and any remaining fibers were cut with a microknife. The underlying vertebral body was exposed through a gap of approximately 3 mm between the cut ends of the spinal cord. The exposed surface of the vertebral body and the lateral recesses were checked under high magnification to ensure that no fibers remained uncut. During the procedure, bleeding was controlled with bipolar electrocautery and by application of sterile gelfoam sponge material (SPONGOSTAN™, Upjohn Co., Kalamazoo, Mich.). Experimental protocols and procedures were in accordance with NIH guidelines for animal research.

Postoperatively, manual expression of the bladder was performed at least twice daily (and up to three times daily in the first 48 hours), until autonomic bladder clearance developed at about the end of the second week. Some animals lost bladder automatism after the electrophysiological studies described below and required manual expression of the bladder until neurogenic control was recovered. The rats were carefully monitored for evidence of urinary tract infection and any other signs of systemic disease. Trimethoprim and sulfamethoxazole (RESPRIM™, Teva Laboratories, Israel, 1 ml/day) was orally administered to each animal in the first postoperative week, and thereafter to any animal showing hematuria. Daily inspection included examination of the laminectomy site for evidence of infection or serous collections, and assessment of the hind limbs for evidence of autophagia or pressure sores. Any severely ill rats were euthanized with an overdose of anesthesia. Such rats, which never exceeded 10% of the number in any treatment group, were excluded for data analysis.

7.1.3 Implantation of Monocytes

Syngeneic peripheral blood monocytes were purified by one-step Percoll fractionation and co-cultured with segments of rat sciatic nerve, as described above. Prior to implantation, the sciatic nerve segments were removed and the cells were washed once and resuspended in fresh DCCM-1 medium and their viability determined.

In one group of animals, fibrin glue from a commercial kit (Octacol-FI5, OMRIX Biopharmaceuticals SA, Brussels, Belgium) was applied to the gap created between the cut ends of the spinal cord. First, 2.5 µl of the BAC component (which contains human fibrinogen 50 mg/ml and other human plasma proteins, as well as tranexamic acid 92 mg/ml) was injected into the gap; then, 2.5 µl of the thrombin component (which contains human thrombin 1000 IU/ml and $CaCl_2$ 40 mM) was injected into the gap. Following administration of fibrin glue, 5 µl of monocyte suspension containing the indicated number of cultured monocytes (or control medium) were administered into the spinal cord parenchyma, distal (i.e. caudal) to the site of injury, with a Hamilton syringe. In a second group of animals, fibrin glue was not used, and the monocyte suspension (or control medium) was injected partly into the gap and partly into the distal parenchyma. No significant difference was observed between these fibrin and non-fibrin treatment groups, which were amalgamated for purposes of data analysis.

In some animals, aFGF (7.5 µg/ml, 5 µl/rat, Calbiochem Megapharm, Cat # 341580) was injected into the distal parenchyma. In all cases, the site of injury was covered with a film of SPONGOSTN™ and the wound was closed in layers.

7.1.4 Evaluation of Motor Function

Motor function was monitored using the open field walking evaluation. Basso et al., 1995, J. Neurotrauma 12: 1–21; Basso et al., 1996, Exp. Neurol. 139: 244–256. Briefly, rats were placed in the middle of a circular enclosure of molded plastic (90 cm diameter, 7 cm wall height) with a smooth, non-slip floor. The rats were stimulated to provoke continuous locomotion during the session, which lasted 4 minutes. A BBB locomotor score was assigned by observing movements involving the trunk, tail and hindlimbs and assigning a score ranging from 0 (no movement) to 22 (normal movement). All hindlimb movements were recorded except for those that were obviously part of a reflex or that were elicited by a touch from the examiner. Special attention was given to hindlimb movements in the lower part of the open field score range.

To evaluate responses dependent on long ascending and descending pathways, contact-placing reflexes were examined. Gale et al., 1985, Exp. Neurol. 88: 123–134; Kerasidis et al., 1987, J. Neurosci. Methods 20: 167–179. Briefly, this response was elicited by light touching (hair bend) without proprioceptive stimulation, on the dorsal and lateral aspects of each foot. A positive contact-placing response involved flexion of the limb to clear the edge of the surface, and subsequent extension and placement of the foot onto the surface for support.

7.1.5 Electrophysiological Studies

One week prior to spinal cord surgery, each rat underwent implantation of screw electrodes extradurally over the sensorimotor cortex of each cerebral hemisphere. Simpson & Baskin, 1987, Neurosurgery 20: 131–137. Briefly, a hole was drilled on each side 1 mm lateral to the midline and 2 mm caudal to the coronal suture until the dura was exposed. A 3/16-inch screw was inserted (2.5 to 3 turns) into the hole. A thin layer of cyanoacrylate glue was applied to the surface of the skull and allowed to dry; the opening was then sealed with dental cement.

During electrophysiological recording, rats were maintained under anesthesia (loading dose of ketamine 40 mg/kg and xylazine 10 mg/kg, administered ip and supplemented with one-third of the loading dose every 30 min). A ground needle electrode was inserted transdermally near the dorsum of the neck. Contralateral muscle motor evoked potentials were elicited by stimulating the corresponding sensorimotor cortex with twin pulses of anodal stimulation from a Grass SD9 stimulator, applying 10 mA of constant current for 0.1 msec (with the cathodic electrode in the hard palate).

At least two motor-evoked potential traces averaging 50 sweeps were recorded from each muscle. A longitudinal skin incision was made along the anterior surface of each hindlimb. The aponeurotic layers were dissected to expose the gastrocnemius, tibialis anterior, quadriceps, adductors and biceps femoris. Monopolar needle electrodes were inserted in the exposed muscles to capture the evoked EMG signals, which were amplified and filtered (Microelectrode AC Amplifier, model 1800, A-M Systems, Everett, Wash.; 100 Hz to 5 kHz bandpass); then digitized (LABVIEW™ for Macintosh, National Instruments, Austin, Tex.); and then stored. After the procedure, the skin was sutured and prophylactic antibiotics were administered for the next few days.

7.1.6 Immunohistochemical Studies

Spinal cord sections were indirectly immunostained for detection of glial fibrillary acidic protein (GFAP), neurofilament protein, or growth-associated protein (GAP-43). Rats were perfused transcardially with saline and 4% paraformaldehyde/PBS solutions. The spinal cords were removed, postfixed in paraformaldehyde, and immersed overnight in 20% sucrose in PBS. Cryosections (20 μm) of macrophage-treated and control spinal cords were prepared, placed on gelatin-coated slides, and dried at room temperature. Sections were fixed in absolute ethanol for 5 min at room temperature, washed several times in double-distilled water, and incubated for 5 min with 0.5% Tween-20 (Sigma, Israel) in PBS to enhance the permeability of the tissue. Sections were incubated at 37° C. with 5% bovine serum albumin in PBS for 30 min, then for 1–2 hours at room temperature with anti-GFAP antibody (Sigma, Israel; 1:100 dilution), anti-GAP-43 antibody (Boerhinger-Mannheim, Germany; 1:100 dilution), or antibody raised against a mixture of 68 kDa and 200 kDA neurofilament proteins (Novocastra Laboratories, UK; 1:50 dilution). After washing three times with 0.05% Tween-20/PBS, the sections were incubated for 30 min at room temperature with fluorescein-conjugated secondary antibodies (Jackson ImmunoResearch, Jackson, Pa.; 1:100 dilution). After extensive washing, the sections were mounted in an antifading agent (1,4 diazabicyclo (2,2,2) octane; Sigma; 22 mM in PBS) and examined by fluorescence microscopy.

7.2 RESULTS

7.2.1 Promotion of Axonal Regeneration in the Transected Spinal Cord by Stimulated Monocytes Rats were subjected to complete spinal cord transection and treated at the time of injury with (1) stimulated monocytes and aFGF; (2) stimulated monocytes alone; (3) (4) control medium and aFGF; and (4) control medium alone. The number of animals in each treatment group and the results obtained are summarized in Table 1.

TABLE 1.

Functional recovery after spinal cord transection

| TREATMENT | | RESULTS | |
|---|---|---|---|
| Stimulated monocytes | aFGF | Number Operated | Number Recovered* |
| 1–4 × $10^5$ | + | 12 | 9 |
| 1–4 × $10^5$ | − | 10 | 3 |
| Nil (CONTROL) | + | 10 | 0 |
| Nil (CONTROL) | − | 21 | 0 |

*Recovery is defined as open field locomotor score > 5

Animals were followed for 19 weeks after spinal cord transection. During the first 8 postoperative weeks, which included a brief initial period of spinal shock lasting about 2 days, all animals showed complete paralysis of the hindlimbs and there was no recovery of locomotor activity (i.e. no BBB locomotor score >5) in any of the treatment or control groups.

After week 8, animals in the control groups (groups 3 and 4) showed either no movement of their hindlimbs or slight movement of one or two joints; the BBB locomotor score was mostly 2 or less, occasionally 4, and never exceeded 5. By contrast, significant recovery was seen in 12 of the 22 animals in the monocyte-treated groups (groups 1 and 2) (ANOVA, p<0.001). Recovery was manifested by extensive movement of all the joints of the hindlimbs, by plantar placement of the paws, and by weightbearing. Six of the treated animals attained a BBB locomotor score of 8 (i.e., sweeping movements with no weightbearing or plantar placement of the paw without weightbearing) and two treated animals attained a BBB locomotor score of 9 (i.e., plantar placement of the paw with weightbearing dorsal stepping and no plantar stepping, and a low-threshold contact placing response, which is considered to be a cortically-integrated reflex). Nine out of 12 animals treated with both monocytes and aFGF (group 1) showed recovery of motor activity, while 3 out of 10 animals treated with monocytes alone (group 2) showed motor recovery. Administering both aFGF and monocytes appeared to increase the proportion of recovered animals rather than the extent of improvement. However, animals that received aFGF alone, without monocytes, showed no motor recovery (i.e. BBB locomotor score did not exceed 5). FIG. 1 (A and B) illustrates progressive recovery of motor function after spinal cord transection in rats treated with monocytes. Additional experiments (data not shown) suggest that the added benefit of aFGF is less marked when animals are treated with greater numbers of monocytes.

In a further treatment group (not shown) fibrin glue was placed in the gap between the cut ends of spinal cord; monocytes and aFGF were then administered into the fibrin (and not into the distal parenchyma). No recovery was seen in this treatment group, suggesting that recovery depends on an adequate number of monocytes being accessible to the transected nerve at the site of the lesion and distal to the site of injury.

Electromyographic studies confirmed that reinnervation of hindlimb muscles occurred in monocyte-treated rats. In normal rats, unipolar stimulation of the hindlimb area of the sensorimotor cortex (a) evokes a late hindlimb electromyographic response (latency 20–30 msec, threshold response at 3–4 mA) and (b) often evokes an early hindlimb electromyographic response (latency 8–10 msec, threshold response at 8 mA). The late EMG response has been related to the corticospinal tract in the rat, on the basis of its conductive properties and lower threshold. Kalderon & Fuks, 1996, Proc. Nat'l Acad. Sci. USA 93: 11185–11190.

In the present study, no late EMG response was seen in any rat (including control and experimental groups) within 2 weeks after spinal cord transection. In control animals examined 12–14 weeks after transection (n=30), no late EMG response was detected in even the most proximal muscle, the quadriceps. By contrast, muscles of monocyte-treated rats (groups 1 and 2) showed varying degrees of recovery of the late EMG response. Complete correlation was observed between the behavioral scores and the electromyographic observations. All animals that showed voluntary locomotor recovery also showed a positive EMG response. Moreover, the locomotor and EMG observations correlated in terms of extent of recovery and bilaterality.

Immunohistochemical studies confirmed the presence of regrowing fibers across the lesioned site. Regrowing fibers were detected using antibodies against the growth-associated protein, GAP-43. Adjacent serial sections of the same tissues were stained with anti-neurofilament antibodies (to detect nerve fibers) and with anti-GFAP antibodies (to detect astrocytes). As shown in FIGS. 2 and 3, the histological observations correlated with the electrophysiological and behavioral results. As seen in FIG. 2 (Aa, Ba), the site of injury was delineated by GFAP staining. See Blaugrund et al., 1993, J. Comp. Neurol. 330: 105–112). In control animals, the site of the lesion was devoid of neurofilament antigens and GAP-43. See FIG. 2 (Bb) & FIG. 3 (Ba, Bb) In monocyte-treated animals with hindlimb EMG responses, by contrast, the site of injury (delineated by GPAF staining) showed intense staining for neurofilament antigens and GAP-43, see FIG. 2 (Ab) & FIG. 3 (Aa, Ab). These results demonstrate that physiological recovery was associated with regrowth of nerve fibers across the site of the lesion. In monocyte-treated animals that did not show recovery, the lesion site did not stain for neurofilament antigens or GAP-43 (not shown).

7.3 DISCUSSION

This example demonstrates that treatment with monocytes led to axonal regeneration, including functional recovery, in rats after complete transection of the spinal cord. Recovery was assessed by voluntary hindlimb motor function, scored in a open field, and by cortically evoked hind limb muscle activity, detected by electromyography. There was excellent correlation between these distinct modes of assessing functional recovery. The motor recovery observed in the present study (values of 8–9 on the 21-point open field locomotor test scale) corresponds to a value of 2 to 3 on the 5-point open field test scale. See Cheng et al., 1996, Science 273: 510–513; Young, 1996, Science 273: 451. The beneficial effect of administering monocytes was enhanced by concurrent treatment with aFGF, although the added benefit of aFGF was less marked upon administration of higher numbers of monocytes. When the monocytes were embedded in fibrin glue, rather than administered in a fluid suspension, no benefit was seen.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of promoting axonal regeneration in an injured spinal cord of a mammal, comprising:
    administering stimulated allogeneic mononuclear phagocytes into the spinal cord parenchyma near the site of injury and distal thereto.

2. The method according to claim 1, wherein said stimulated allogeneic mononuclear phagocytes are allogeneic mononuclear phagocytes which have been cultured together with skin or at least one nerve segment, medium conditioned by skin or at least one nerve segment, or medium to which has been added transforming growth factor-beta (TGF-β), β-interferon (IFN-β), γ-interferon (IFN-γ), tumor necrosis factor α (TNF-α), interleukin 2 (IL-2), interleukin 3 (IL-3), interleukin 4 (IL-4), interleukin 10 (IL-10), monocyte chemotactic and activating factor (MCAF), macrophage colony stimulating factor (M-CSF), granulocyte-macrophage colony stimulating factor (GM-CSF), colony stimulating factor 1 (CSF-1), neurotrophic factor 3 (NT-3), nerve growth factor (NGF), brain-derived neurotrophic factor (BDNF), lipid A, the tripeptide fMet-Leu-Phe, muramyl dipeptide (MDP), the ionophore A23187, or vitamin D3 binding protein.

3. The method according to claim 2, in which said allogeneic mononuclear phagocytes have been cultured in medium to which has been added IL-4, IL-10, or both IL-4 and IL-10.

4. The method according to claim 2, in which said allogeneic mononuclear phagocytes have been cultured together with skin or with medium conditioned by skin.

5. The method according to claim 4, which said skin is autologous to said mammal.

6. The method according to claim 2, in which said allogeneic mononuclear phagocytes have been cultured together with at least one nerve segment or with medium conditioned by at least one nerve segment.

7. The method according to claim 6, in which said nerve segment is a segment of a peripheral nerve.

8. The method according to claim 7, in which said nerve segment is a segment of an allogeneic peripheral nerve.

9. The method according to claim 1, in which said allogeneic mononuclear phagocytes are autologous mononuclear phagocytes.

10. The method according to claim 9, in which said autologous mononuclear phagocytes have been cultured together with skin or with medium conditioned by skin.

11. The method according to claim 10, in which said skin is autologous to said mammal.

12. The method according to claim 1, in which said mononuclear phagocytes are monocytes.

13. The method according to claim 1, in which said mononuclear phagocytes are macrophages.

14. The method according to claim 13, in which said mononuclear phagocytes are macrophages obtained from a serosal cavity, alveolar macrophages, macrophages obtained from the liver, spleen or thymus, or macrophages derived from culturing macrophage precursors obtained from bone marrow or from blood.

15. The method according to claim 1, in which said mononuclear phagocytes are not microglia and are not derived by culture from brain-derived mixed glial cells.

16. The method according to claim 1, in which said mononuclear phagocytes are dendritic cells.

17. The method according to claim 1, in which said mammal is a human being.

18. The method according to claim 1, further comprising administering to the mammal at least one anti-inflammatory agent.

19. The method according to claim 18, wherein said anti-inflammatory agent is a steroid, a non-steroidal anti-inflammatory agent (NSAID), or the tripeptide Thr-Lys-Pro.

20. The method according to claim 1, further comprising administering to the spinal cord parenchyma at least one of the following adjuvant factors: acidic fibroblast growth factor (aFGF), transforming growth factor-beta (TGF-β), interleukin 6 (IL-6), nerve growth factor (NGF), neurotrophic factor 3 (NT-3), neurotrophic factor 4 (NT-4), neurotrophic factor 5 (NT-5) and brain-derived neurotrophic factor (BDNF).

21. The method according to claim 20, wherein said adjuvant factor is acidic fibroblast growth factor (aFGF).

22. The method according to claim 21, wherein said aFGF is administered at or near said site of injury.

23. The method according to claim 1, wherein said injury has resulted in impaired motor function.

24. The method according to claim 23, wherein said administering results in improvement of said impaired motor function.

25. A method of promoting axonal regrowth after injury or disease that results in or is accompanied by axonal damage in the central nervous system (CNS) of a mammal, comprising:
(a) culturing a first preparation of allogeneic mononuclear phagocytes together with at least one tissue or with at least one cell type, or with medium conditioned by at least one tissue or at least one cell type, or with medium to which has been added at least one biologically active agent;
(b) after the step of culturing, measuring the phagocytic activity, the nitric oxide production, or both the phagocytic activity and the nitric oxide production of said first preparation of allogeneic mononuclear phagocytes, whereby an increase in one or both of phagocytic activity and nitric oxide production occurs to identify a stimulatory tissue, stimulatory cell type or stimulatory biologically active agent;
(c) culturing a second preparation of allogeneic mononuclear phagocytes together with said stimulatory tissue or stimulatory cell type, with medium conditioned by said stimulatory tissue or stimulatory cell type, or with medium to which has been added said stimulatory biologically active agent, so as to produce a preparation of stimulated mononuclear phagocytes; and
(d) administering at least a portion of said preparation of stimulated mononuclear phagocytes into the CNS at or near the site of axonal damage.

26. A method of promoting axonal regrowth after injury or disease that results in or is accompanied by axonal damage in the central nervous system (CNS) of a mammal, comprising:
administering stimulated allogeneic mononuclear phagocytes into the CNS at or near the site of axonal damage.

27. The method according to claim 26, wherein said stimulated allogeneic mononuclear phagocytes are allogeneic mononuclear phagocytes which have been cultured together with skin or at least one nerve segment, medium conditioned by skin or at least one nerve segment, or medium to which has been added transforming growth factor-beta (TGF-β), β-interferon (IFN-β), γ-interferon (IFN-γ), tumor necrosis factor α (TNF-α), interleukin 2 (IL-2), interleukin 3 (IL-3), interleukin 4 (IL-4), interleukin 10 (IL-10), monocyte chemotactic and activating factor (MCAF), macrophage colony stimulating factor (M-CSF), granulocyte-macrophage colony stimulating factor (GM-CSF), colony stimulating factor 1 (CSF-1), neurotrophic factor 3 (NT-3), nerve growth factor (NGF), brain-derived neurotrophic factor (BDNF), lipid A, the tripeptide fMet-Leu-Phe, muramyl dipeptide (MDP), the ionophore A23187, or vitamin D3 binding protein.

28. The method according to claim 27, in which said allogeneic mononuclear phagocytes have been cultured in medium to which has been added IL-4, IL-10, or both IL-4 and IL-10.

29. The method according to claim 27, in which said allogeneic mononuclear phagocytes have been cultured together with skin or with medium conditioned by skin.

30. The method according to claim 29, in which said skin is autologous to said mammal.

31. The method according to claim 27, in which said allogeneic mononuclear phagocytes have been cultured together with at least one nerve segment or with medium conditioned by at least one nerve segment.

32. The method according to claim 31, in which said nerve segment is a segment of a peripheral nerve.

33. The method according to claim 32, in which said nerve segment is a segment of an allogeneic peripheral nerve.

34. The method according to claim 26, in which said allogeneic mononuclear phagocytes are autologous mononuclear phagocytes.

35. The method according to claim 34, in which said autologous mononuclear phagocytes have been cultured together with skin or with medium conditioned by skin.

36. The method according to claim 35, in which said skin is autologous to said mammal.

37. The method according to claim 26, in which said mononuclear phagocytes are monocytes.

38. The method according to claim 26, in which said mononuclear phagocytes are macrophages.

39. The method according to claim 38, in which said mononuclear phagocytes are macrophages obtained from a serosal cavity, alveolar macrophages, macrophages obtained from the liver, spleen or thymus, or macrophages derived from culturing macrophage precursors obtained from bone marrow or from blood.

40. The method according to claim 26, in which said mononuclear phagocytes are not microglia and are not derived by culture from brain-derived mixed glial cells.

41. The method according to claim 26, in which said mononuclear phagocytes are dendritic cells.

42. The method according to claim 26, in which said mammal is a human being.

43. The method according to claim 26, further comprising administering to the mammal at least one anti-inflammatory agent.

44. The method according to claim 43, wherein said anti-inflammatory agent is a steroid, a non-steroidal anti-inflammatory agent (NSAID), or the tripeptide Thr-Lys-Pro.

45. The method according to claim 26, further comprising administering into the CNS at or near the site of axonal damage at least one of the following adjuvant factors: acidic fibroblast growth factor (aFGF), transforming growth factor-beta (TGF-β), interleukin 6 (IL-6), nerve growth factor (NGF), neurotrophic factor 3 (NT-3), neurotrophic factor 4 (NT-4), neurotrophic factor 5 (NT-5) and brain-derived neurotrophic factor (BDNF).

46. The method according to claim 45, wherein said adjuvant factor is acidic fibroblast growth factor (aFGF).

* * * * *